(12) United States Patent
Martin et al.

(10) Patent No.: US 6,509,367 B1
(45) Date of Patent: Jan. 21, 2003

(54) PYRAZOLE CANNABINOID AGONIST AND ANTAGONISTS

(75) Inventors: Billy R. Martin, Richmond, VA (US); Raj K. Razdan, Gloucester, MA (US); Anu Mahadevan, Woburn, MA (US)

(73) Assignees: Virginia Commonwealth University, Richmond, VA (US); Organix, Inc., Woburn, MA (US)

( * ) Notice: Subject to any disclaimer, the term of this patent is extended or adjusted under 35 U.S.C. 154(b) by 0 days.

(21) Appl. No.: 09/682,577

(22) Filed: Sep. 22, 2001

(51) Int. Cl.$^7$ .............................................. A61K 31/415
(52) U.S. Cl. ..................... 514/406; 514/403; 548/374.1
(58) Field of Search .................................. 514/406, 341

(56) References Cited

U.S. PATENT DOCUMENTS 5,462,960 A * 10/1995 Barth et al. .................. 514/406
6,344,474 B1 * 2/2002 Maruani et al. ............ 514/406

* cited by examiner

*Primary Examiner*—Dwayne C. Jones
(74) *Attorney, Agent, or Firm*—Whitham, Curtis & Christofferson, PC

(57) ABSTRACT

Disclosed are pyrazole derivatives of formula I:

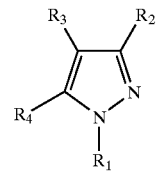

Where $R_1$, $R_2$, $R_3$, and $R_4$ are defined as in the specification described. These compounds are antagonists of the brain cannabinoid (CB-1) receptors and could be used as active gradients in pharmaceutical preparations to block or inhibit cannabinoid receptors in mammals.

18 Claims, 6 Drawing Sheets

PYRAZOLE CANNABINOID AGONIST AND ANTAGONISTS

FEDERAL RESEARCH STATEMENT

This invention was made in part by National Institutes on Drug Abuse with grant numbers DA-09789 and DA-03672. The government may have certain rights in this invention.

BACKGROUND OF INVENTION

1. Field of Invention

This invention relates to cannabinoids, and particularly relates to agonists and antagonists of cannabinoid that interact with brain cannabinoid ($CB_1$) receptor. The invention includes analogs of SR14176A, a $CB_1$ antagonist that blocks the actions of cannabinoids both in vivo and in vitro, as well as the use of these analogs.

2. Description of Prior Art

Cannabinoids are compounds derived from the cannabis sativa plant which is commonly known as marijuana. The most active chemical compound of the naturally occurring cannabinoids is tetrahydrocannabinol (THC), particularly $\Delta^9$-THC (FIG. 1b).

Marijuana based medicines have been known for centuries and have been a mainstay of many folk, herbal remedies. Many beneficial pharmacological properties can be attributed to marijuana. Among them are analgesia, lowering blood and intra-ocular pressure, and anti-emetic activity in both mammals and man. Beneficial effects of marijuana as well as its negative effects have been well documented. The negative pharmacological effects associated with marijuana (and later shown to be associated with THC) include psychological distortions of perception, loss of short-term memory, loss of motor coordination, sedation, and euphoria. Long term use of marijuana is considered by many to lead to addiction.

Two distinct types of receptors that bind both the naturally occurring and synthetic cannabinoids have been discovered. They are designated as $CB_1$, the receptor located in the central nervous system, and as $CB_2$, the receptor found in peripheral tissues. It is generally agreed that much of the cannabinoid pharmacology is associated with its effects on the central nervous system, and that these effects are directly related to the action of the $CB_1$ receptor.

Synthetic and natural compounds, which are agonists of the $CB_1$ receptor, demonstrate the expected experimental and human pharmacology, while closely related compounds that bind poorly to $CB_1$ do not (Mechoulam et al.1994). Compounds that bind to brain cannabinoid ($CB_1$) receptors show a large degree of diversity in chemical structure. These compounds include classical tricyclic and bicyclic cannabinoids, aminoalkylindoles, indoles, pyrroles, and anandamides. Each of these compounds shares a similar profile of pharmacological activity in vivo with the prototypic tricyclic cannabinoid, $\Delta^9$-tetrahydrocannabinol ($\Delta^9$-THC), albeit they differ in potency and in efficacy in individual assays (Adams et al., 1995; Compton et al., 1992, 1993; Wiley et al., 1998). These in vivo cannabimimetic effects include hypoactivity, hypothermia, antinociception and catalepsy in mice (Martin et al., 1991; Smith et al., 1994), $\Delta^9$-THC-like discriminative stimulus effects in rats and monkeys (see Wiley, 1999 for review), and static ataxia in dogs (Lichtman et al., 1998).

After the elucidation of THC structure, several synthetic compounds were prepared and found to be effective for the treatment of pain in cancer patients, among these are: nabilone, naboctate and levonantradol. Although these drugs are useful, they have to a greater or lesser extent some of the negative pharmacological properties of THC, and, thus, their general use is limited.

Non-cannabinoid analogs have also been developed. For example, Pacheco et al., reveals WIN 55,212-2, an aminoalkylindole (Pacheco et al., 1991, and Compton et al., 1992). U.S. Pat. No. 5,747,542 (Cullinan et al.) discloses aryl-benzo[b]thiophene and benzo[b]furan compounds. European Patent EP0576357 (Barth et al.) reveals halo-aryl pyrazoles, including SR 141716A.

SR 141716A (FIG. 1a) has been shown to block the actions of cannabinoids in in vivo and in vitro models (Rinaldi-Carmona et al., 1994). SR 141716A selectively binds to cannabinoid $CB_1$ receptors without producing cannabimimetic activity in vivo (Compton et al., 1996), suggesting that binding and activation of cannabinoid receptors are separable events. Consequently, structure-activity relationship (SAR) studies with analogs of this antagonist provide a unique opportunity to compare the structural requirements for binding and antagonist activity to those required for binding and agonist efficacy. To date, only a couple of studies have been published which systematically examined the SAR of cannabinoid $CB_1$ antagonists (Lan et al., 1999; Thomas et al., 1998). While both of these studies reported $CB_1$ binding values for SR 141716A analogs, neither involved measurement of in vivo activity of the compound alone and in combination with a cannabinoid agonist.

There is much debate over whether marijuana use should be legalized in certain cases, such as its use in cancer patients for ameliorating the nausea induced by chemotherapy or to lower intra-ocular pressure in glaucoma patients. The effects of marijuana are thought to be due to its actions at $CB_1$ receptors. Therefore, the logical alternative to marijuana is a synthetic cannabinoid agonist. Considering the beneficial effects of cannabinoids, it would be highly desirable to have an effective $CB_1$ receptor agonist that produces fewer adverse effects than THC. The discovery of cannabinoid receptors and their endogenous ligands, such as anandamide and 2-arachidonyl-glycerol, led to the realization that an endogenous cannabinoid system exists. Therefore, an overactive endogenous cannabinoid system would be expected to produce THC-like effects, such as appetite stimulation and disruption of cognitive and. memory processes. The development of cannabinoid antagonists therefore will have therapeutic potential in treating obesity, memory deficits in disease states and psychopathology such as schizophrenia.

BRIEF SUMMARY OF INVENTION

This invention provides a compound of formula I:

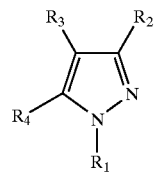

(I), wherein $R_1$ is a phenyl that is unsubstituted or substituted one or more times by a halogen, or a $C_{1-7}$ alkyl;

$R_2$ is
an ether of formula

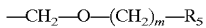
—CH$_2$—O—(CH$_2$)$_m$—R$_5$ where $R_5$ is a heterocyclic, a $C_{4-7}$ cycloalkyl, or an aryl, and m is 1 or 2,
an amide of formula

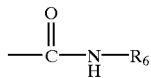

where $R_6$ is a $C_{1-8}$ alkyl, a $C_{1-6}$ haloalkyl, or a piperidine, a ketone of formula

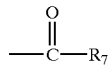

where $R_7$ is a $C_{1-6}$ alkyl, or
an alcohol of formula

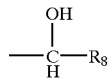

where $R_8$ is $C_{1-6}$ alkyl;
$R_3$ is a methyl, a hydrogen, or a halogen; and
$R_4$ is a $C_{1-8}$ alkyl or a phenyl that is unsubstituted or substituted one or more times by a halogen, or a $C_{1-7}$ alkyl;
provided $R_6$ is other than a $C_{1-3}$ alkyl, where $R_1$ and $R_4$ are independently a phenyl that is unsubstituted or substituted one or more times by a halogen, or a unbranched $C_{1-3}$ alkyl;
further provided $R_3$ is other than a methyl, where $R_6$ is a piperidine.

More specifically, the present invention involves the synthesis of a series of analogs of SR 141716A and the development of analogs with high receptor binding affinity and potential agonist and antagonist effects.

The invention also provides treatments which comprise administering an effective amount of a compound of formula I and pharmaceutical formulations which include a novel compound of formula (I) as an active ingredient in combination with a pharmaceutically acceptable carrier, diluent, or excipient to antagonize one or more of the actions of endogenous cannabinoids at brain cannabinoid (CB$_1$) receptors in mammals.

DETAILED DESCRIPTION OF THE INVENTION

Figure 1B:
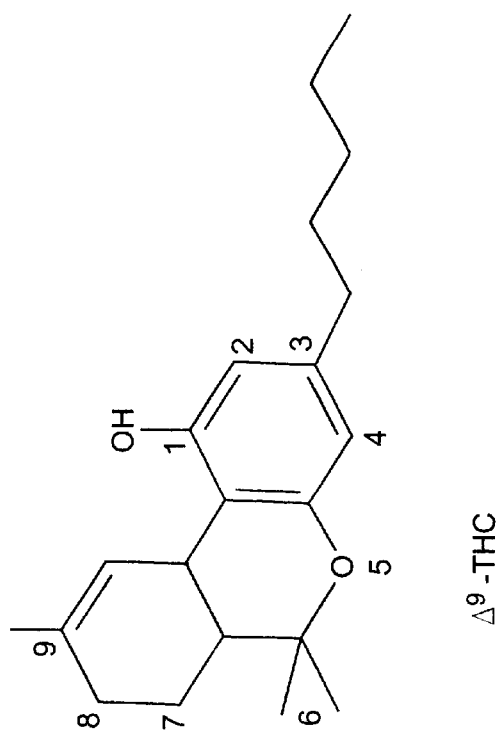
FIG. 1b is the chemical structure of $\Delta^9$-THC.

An area of receptor recognition that is crucial for all known CB$_1$ agonists is a lipophilic side chain (e.g., THC and anandamides) or comparable moiety (e.g., nitrogen substituent of indole-derived cannabinoids) (Huffman et al., 1994; Martin et al., 1991; Thomas et al., 1996; Wiley et al., 1998). Changes in the length, branching, and flexibility of this side chain affects CB$_1$ receptor binding affinity and in vivo potency of cannabinoid agonists (Compton et al., 1993; Huffman et al., 1997; Martin et al., 1999).

Without being bound by the theory, the present invention is based upon the discovery that SR141716A binds to CB$_1$ receptors and competitively antagonizes many of the CB$_1$ receptor-mediated effects of cannabinoids. Synthesis of an antagonist, SR141716A, that selectively binds to brain cannabinoid (CB$_1$) receptors without producing cannabimimetic activity in vivo suggests that recognition and activation of cannabinoid receptors are separable events. The structure of SR141716A may contain regions of overlap with those of cannabinoid agonists. Molecular modeling suggests a possible superpositioning of the para-position of the 5-substituent in SR141716A with the pentyl side chain in $\Delta^9$-THC (Thomas et al., 1998).

Definitions and Nomenclatures
As used herein:
The term "alkyl" means unbranched or branched saturated hydrocarbon chain containing 1 to 12 carbon atoms, such as methyl, ethyl, propyl, isopropyl, s-butyl; tert-butyl, isobutyl, tert-butyl, n-hexyl, n-octyl, n-dodecyl, and the like. "Cycloalkyl" means a monovalent saturated carbocyclic having from three to eight carbon atoms, e.g., cyclopropyl, 2-methylcyclopropyl, cyclobutyl, 3-ethylcyclobutyl, cyclopentyl, cyclohexyl, cycloheptyl, cyclooctyl.

"Halogen" includes F, Cl, Br, and I.
"Halo" denotes fluoro, chloro, bromo, or iodo, unless otherwise indicated.

"Haloalkyl" means alkyl as defined above substituted by 1 to 5 halogen atoms in any position, for example trifluoromethyl, 1-fluoroethyl, pentachloroethyl, 1,1,1-trichloro-n-propyl, 1-bromo-n-butyl, 1,2-dibromo-3-methylpentane, 1-iodooctane, and the like.

"Fluoroalkyl" means alkyl as defined above substituted by 1 to 5 fluorine atoms in any position, for example trifluoromethyl, 1-fluoroethyl, pentafluoroethyl, 1,1,1-trifluoro-n-propyl, 1-fluoro-n-butyl, 1,2-difluoro-3-methylpentane, 1-fluorooctane, and the like.

The term "heterocyclic" means a ring structure having one or two heteroatoms m such as nitrogen, oxygen, and sulfur, and includes, for example, pyrrolidine, pyrrole, pyrazole, imidazole, piperidine, furan, thiophene, oxazole, thiazole, pyrimidine, and the like.

The term "aryl" as used herein means a monocyclic aromatic ring, or a 9 to 14 membered bicyclic or tricyclic ring system in which at least one ring is aromatic in nature, and includes one substituted one or more times by a halogen, a alkyl group. Examples of aryl groups include, but are not limited to, phenyl, naphthalene, anthracene, phenanthrene.

"Phenyl" includes mono-, di- or tri-substitution on the aromatic benzene ring by halogen, lower alkoxy, lower alkoxymethyl, hydroxy, lower alkyl, amino, lower alkylamino, or lower alkylthio groups. For example, alkylphenyl means phenyl attached to an alkyl group as defined above, for example methylphenyl(benzyl), propylphenyl, and the like.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It is intended that the definition of any substituent (e.g., $R_5$) in a particular molecule be independent of its definition elsewhere in the molecule. Thus, —N($R_5$)$_2$ represents —NHH, —NHCH$_3$, —NHC$_6$H$_5$, etc.

Abbreviations

The abbreviations used in this invention are as follows:

Anandamide=arachidonylethanolamide

CB$_1$ receptor=brain cannabinoid receptor

CP 55,940=(−)-cis-3-[2-hydroxy-4(1,1-dimethyl-heptyl) phenyl]-trans-4-(3-hydroxypropyl)cyclohexanol GTPgammaS=guanosine-5'-O-(3-[$^{35}$S]thio)-triphosphate MPE=maximal possible antinociceptive effect RI=ring immobility RT=rectal temperature SA=spontaneous activity SAR=structure-activity relationship SR141716A=N-(piperidin-1-yl)-5-(4-chlorophenyl)-1-(2, 4-dichlorophenyl)-4-methyl-1H-pyrazole-3-carboxamide hydrochloride $\Delta^9$-THC=$\Delta^9$-tetrahydrocannabinol WIN 55,212-2=R-(+)-(2,3-dihydro-5-methyl-3-[(4-morpholinyl)methyl]pyrol(1,2,3,-de]-1,4-benzoxazin-6-yl)(1-naphthalenyl)methanone monomethane-sulfonate

DISCLOSURE OF THE INVENTION

Figure 1A:
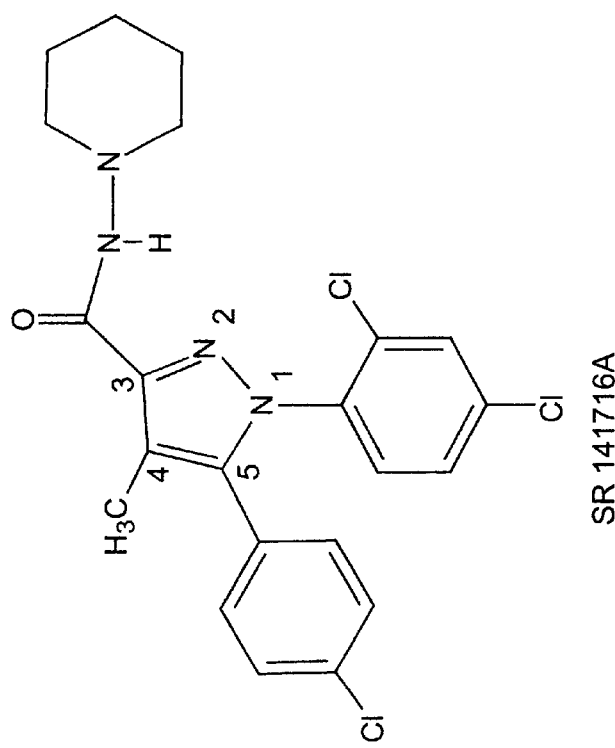
FIG. 1a is the Chemical structure of SR141716A with points of substituent attachment marked by numbers surrounding the pyrazole core: 1(dichlorophenyl group), 3(carboxyamide and piperidine groups), 4(methyl group), and 5(chlorophenyl group).

FIG. 1a shows the structure of SR 141716A. One objective of the present invention is to provide the synthesis of a series of analogs of SR 141716A that retain a central pyrazole structure with manipulation of one of four other areas of the molecule: (a) substitution for carboxamide and/or piperidine substituent (3-substituent substitution); (b) substitution for the 2,4-dichlorophenyl group (1-substituent substitution); (c) substitution for chlorophenyl group (5-substituent substitution); or (d) substitution for the methyl (4-substituent substitution). Cannabinoid receptor binding affinities were determined, followed by in vivo testing, including hypomobility, antinociception, and hypothermia in mice. Selected compounds with binding affinity ($K_i$) less than 100 nM were further tested in combination with active dose(s) of $\Delta^9$-THC in order to evaluate potential antagonist effects.

The preferred embodiments of synthesizing these analogs are illustrated in Schemes 1–4, shown in FIGS. 2–5. They are addressed in detail in the Synthesis Approaches under the EXAMPLE section. It will be apparent to one skilled in the art that various modifications and substitutions may be made to the invention disclosed herein without departing from the scope and the spirit of the invention. Accordingly, the examples in FIGS. 2–5 are intended to illustrate but not limit the present invention.

The representative examples of analogs are shown in Table 1–4. The preferred compounds having formula I are realized as follows:

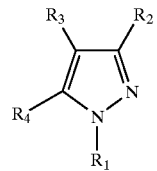

wherein $R_1$ is a phenyl that is unsubstituted or substituted one or more times by a halogen, or a $C_{1-7}$ alkyl;

$R_2$ is an ether of formula

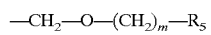

where $R_5$ is a heterocyclic, a $C_{4-7}$ cycloalkyl, or an aryl, and m is 1 or 2, an amide of formula

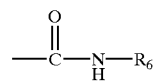

where $R_6$ is a $C_{1-8}$ alkyl, a $C_{1-6}$ haloalkyl, or a piperidine, a ketone of formula

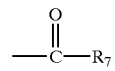

where $R_7$ is a $C_{1-6}$ alkyl, or an alcohol of formula

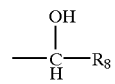

where $R_8$ is $C_{1-6}$ alkyl;

$R_3$ is a methyl, a hydrogen or a halogen; and $R_4$ is a $C_{1-8}$ alkyl or a phenyl that is unsubstituted or substituted one or more times by a halogen, or a $C_{1-7}$ alkyl;

provided $R_6$ is other than a $C_{1-3}$ alkyl, where $R_1$ and $R_4$ are independently a phenyl that is unsubstituted or substituted one or more times by a halogen, or a unbranched $C_{1-3}$ alkyl;

further provided $R_3$ is other than a methyl, where $R_6$ is a piperidine.

Tables 1–5 set forth the Structure-Activity Relations for agonist activity in mice. The most significant effects of cannabimimetic activity were observed when the 3-substituent of SR141716A was replaced with an alkyl amide or ketone group. None of the 3-substituted analogs produced antagonist effects when tested in combination with 3 mg/kg $\Delta^9$-tetrahydrocannabinol ($\Delta^9$-THC). The Structure-Activity Relationship for antagonist activity in mice is illustrated in Table 6 and FIG. 6. Antagonistic effects of $\Delta^9$-THCs without accompanying agonist or partial agonist effects was observed with substitutions at positions 1, 4, and 5. These results suggest that the structural properties of 1- and 5-substituents are primarily responsible for the antagonist activity of SR141716A.

Structure-activity relationships (SAR) of SR141716A analogs presented here and elsewhere (Lan et al., 1999; Thomas et al., 1998) are consistent with this proposed alignment. Retention of the phenyl group is critical for receptor affinity and antagonism, as illustrated with O-1559 which had an alkyl group at position 5 rather than a phenyl. Substitution of the para-portion of the phenyl substituent is also important. Deletion of the p-chloro group (Lan et al., 1999) greatly decreased affinity whereas substitution of an alkyl group or an iodo/bromo (Thomas et al., 1998) enhanced affinity. Lengthening of the pentyl side chain of $\Delta^9$-THC (Martin et al., 1999), methylation at the first or second carbon of the chain (Huffman et al., 1997), and halogenation at the terminal end of the chain (Charalambous et al., 1991) resulted in analogs that were agonists in vivo and that had enhanced $CB_1$ affinity compared to the parent compound.

The preferred compounds are realized when R1 and R4 are independently a phenyl, and R2 is ether or an amide. Specifically, the most preferred compounds are O-889, O-1043, O-1270, O-1398, O-1302, O-1690, O-1691, and O-1704.

Utilities

The ability of the compounds of formula I to mimic the actions of the cannabinoids makes them useful for preventing or reversing the symptoms that can be treated with cannabis, some of its derivatives, and synthetic cannabinoids in a human subject. Thus, compounds of formula I are useful, but not limited, to treat or ameliorate in mammals and especially in humans: (1) various ocular disorders such as glaucoma; (2) pulmonary disorders including diseases such as asthma, chronic bronchitis and related airway diseases; (3) allergies and allergic reactions such as allergic rhinitis, contact dermatitis, allergic conjunctivitis and the like; (4) inflammation such as arthritis or inflammatory bowel disease; (5) pain; (6) disorders of the immune system such as lupus, AIDS, etc.; (7) allograft rejection; (8) central nervous system diseases such as Tourette's syndrome, Parkinson's disease, Huntingdon's disease, epilepsy, various psychotic afflictions such as depression, manic depression, etc.; (9) vomiting, and nausea and vertigo, especially in the case of chemotherapy patients.

One skilled in the art will appreciate that compounds of formula I that act as cannabinoid antagonists are useful, but not limited to, treatment of (1) obesity; (2) cognitive impairment such as in Alzheimer's disease; (3) schizophrenia; and (4) epilepsy.

It will be also understood that in the discussion of methods of treatment that references to the compounds of Formula I is meant to also include the pharmaceutically acceptable salts.

Dose Ranges

The magnitude of therapeutic dose of a compound of Formula I will, of course, vary with the nature of the severity of the condition to be treated, with the particular compound of Formula I, and with its route of administration. The optimal dosage may, of course, vary upon the clinician's judgment. It will also vary according to the age, weight and response of the individual patient. An effective dose of the active component may be tailored to the individual needs of the patient and determined by the clinician after a consideration of all criteria.

The preferred dosage range of the present invention is about 0.1–10 mg of compound per kg of mammal by weight. Dosage forms include tablets, troches, dispersions, suspensions, solutions, capsules, creams, ointments, aerosols, and the like. Any route of administration may be employed that is suitable for mammals. For example, oral, parenteral, and topical may be employed. The preferred administration route is intravenously (i.v.) injection.

Pharmaceutical Compositions

The pharmaceutical compositions of the present invention comprise a compound of Formula I as an active ingredient, or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. Suitable pharmaceutically acceptable carriers and their formulations are described in standard formulation treaties, e.g., Remington's Pharmaceutical Science by E. W. Martin. See also Wang Y J and Hanson M A. "Parental Formulations of Proteins and Peptides: Stability and Stabilizer." Journals of Parental Sciences and Technology, Technical Report No. 10, Supp. 42: 2S (1988).

The compositions include compositions suitable for oral, parenteral, and ocular (ophthalmic) delivery. They may be conveniently presented in unit dosage form and be prepared by any of the methods well known in the art of pharmacy. Those of ordinary skill in the art will understand and appreciate the techniques appropriate for determining whether an active ingredient has a desired efficacious outcome based upon the needs of the artisan.

Combinations with Other Drugs

In addition to the compounds of Formula I, the pharmaceutical compositions of the present invention can also contain other active ingredients or pro-drugs thereof. These other active species may be beta-blockers (e.g., timolol), topical carbonic anhydrase inhibitors (e.g., Dorzolamide), systemic carbonic anhydrase inhibitors (e.g., acetolamide), and cholinergic agents (e.g., pilocarpine and its derivatives). The weight ratio of the compound of the Formula I to the second active ingredient may be varied and will depend upon the effective dose of each ingredient. Generally, an effective dose of each will be used. The combinations may, of course, be tailored to the individual needs of the patient and are best determined by skilled practitioners, such as physicians.

EXAMPLES 1

Synthetic Approaches

Compounds of the present invention can be prepared according to the following non-limiting methods. These compounds may be readily prepared according to a variety of synthetic manipulations, all of which would be familiar to one skilled in the art. Accordingly, the specific examples that follow should not be considered as limiting the invention, but merely to illustrate the best mode of synthesis at this time.

Synthesis of SR74776A analogs

Figure 2:
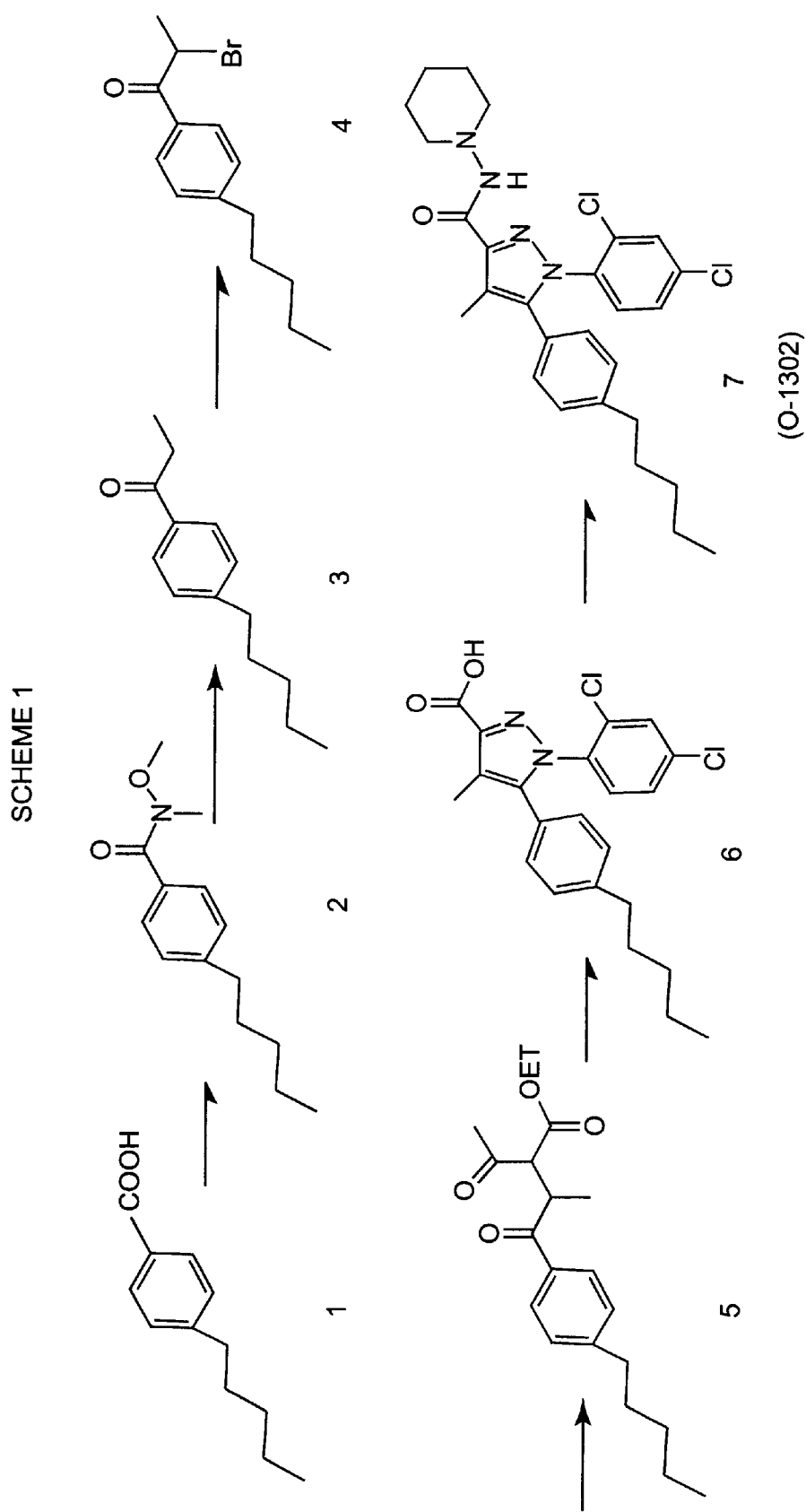
FIG. 2. Synthesis scheme 1.

FIG. 2 shows the preferred method of synthesizing O-1302 (antagonist 7) in Scheme 1. The synthesis of the antagonist 7 (O-1302) was achieved in an overall yield of 9.8% using a similar sequence as reported by us for the synthesis of the antagonist SR14176A (Dutta et al., 1995). In short, the commercially available 4-n-pentylbenzoic acid (1)

was converted to the benzamide 2 via its acid chloride (oxalyl chloride/$CH_2Cl_2$), which on treatment with N,O-dimethyl-hydroxylamine hydrochloride formed 2 (98%). A Grignard reaction with EtMgBr/THF transformed 2 to the ketone 3 (98%), which on bromination ($Br_2$/AcOH) gave the bromoketone 4 (72%). Treatment of 4 with the anion of ethylacetoacetate (NaH/THF) formed 5 (54%) which on treatment with a 2,4-dichlorodiazoniumchloride solution, in the presence of Na/ethanol at 0° C., followed by alcoholic NaOH solution reflux, gave the pyrazole derivative 6 (32%). The acid chloride of 6 (oxalyl chloride/$CH_2Cl_2$) was treated with 1-aminopiperidine/$Et_3N$/$CH_2Cl_2$ to afford 7 (O-1302) in 82% yield.

Figure 3:
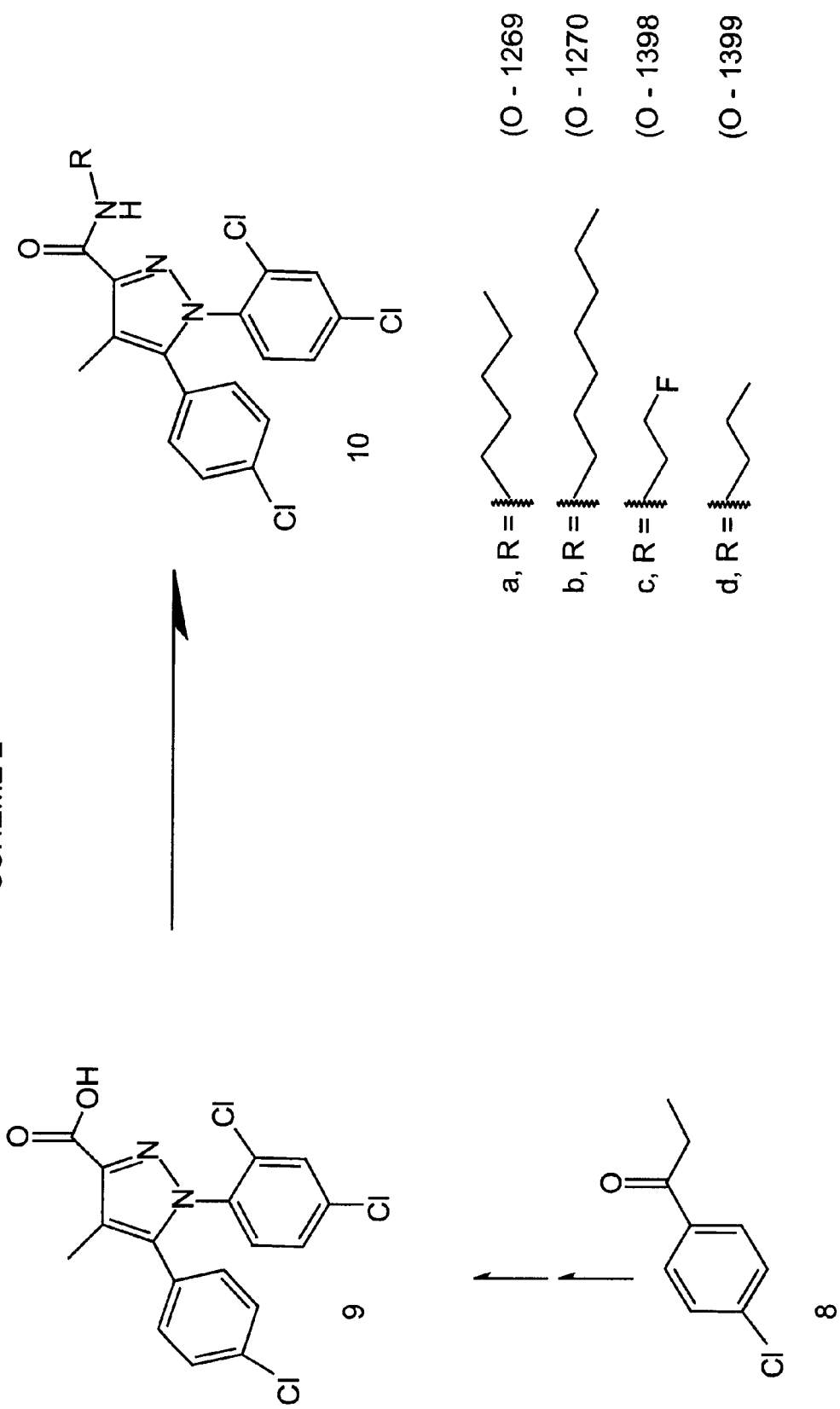
FIG. 3. Synthesis scheme 2.

FIG. 3 shows the preferred method of synthesizing the 3-substituted analogs 10a–d (Scheme 2). The 3-substituted analogs 10a–d were synthesized from the acid 9 by conversion to its acid chloride and subsequent treatment with the appropriate amines as in the conversion of 6 to 7. The acid 9 was prepared from 4'-chloropropiophenone (8) using our published procedure (Dutta et al., 1995). Thus treatment of the acid chloride of 9 with n-pentylamine gave 10a (O-1269). Similarly 10b (1270), 10c (O-1398) and 10d (O-1399) were formed in 39, 54, 63 and 69% yields respectively.

Figure 4:
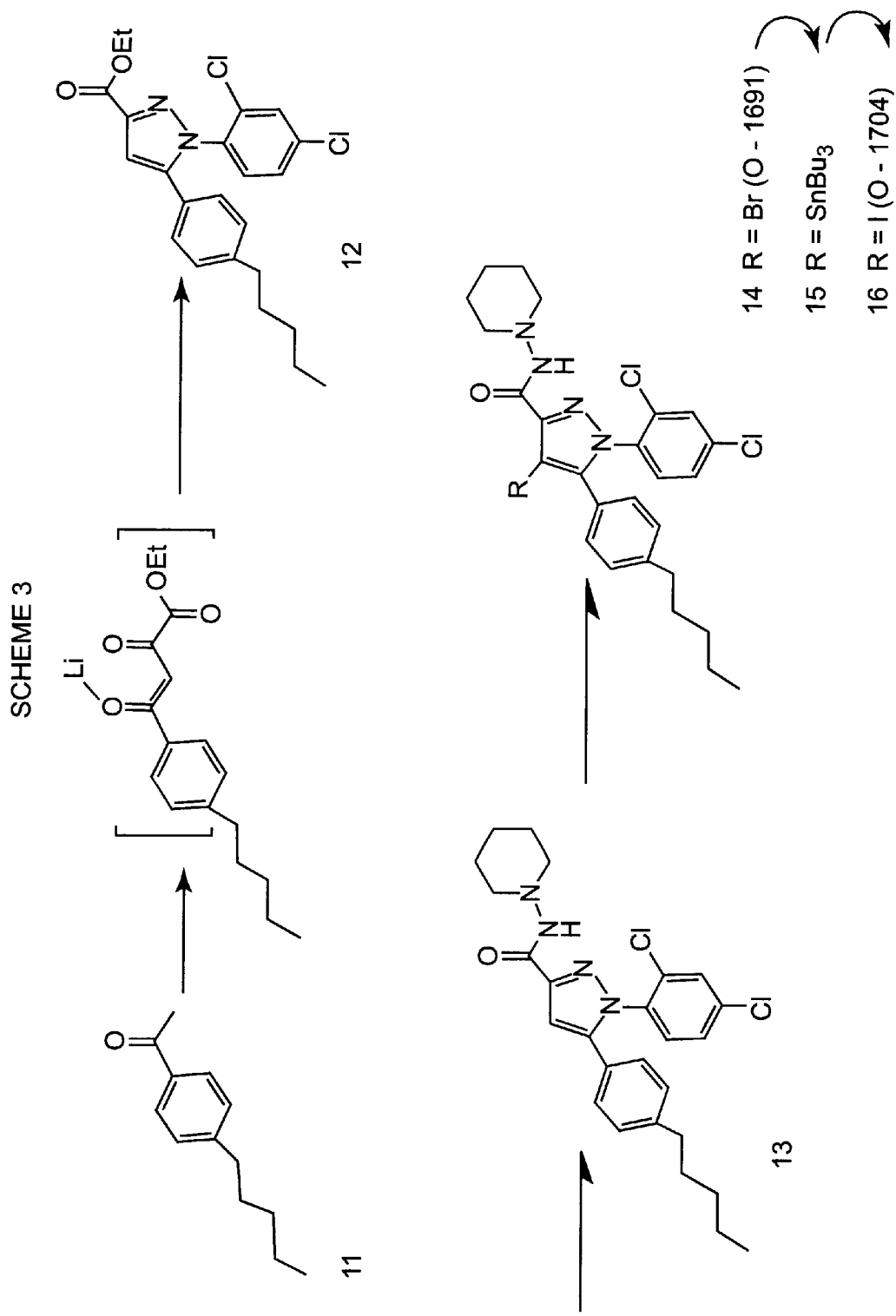
FIG. 4. Synthesis scheme 3.

FIG. 4 shows the preferred method of synthesizing the 4-substituted analogs 14 (O-1691) and 16 (O-1704) in Scheme 3. The antagonists 14 and 16 were synthesized from 4'-n-pentylacetophenone 11 (prepared from 4'-bromoacetophenone) in overall yields of 35 and 13% respectively. Using a literature procedure, compound 11 was allowed to react with diethyloxalate in the presence of lithiumhexamethyldisilazide in ether to give the product as the lithium salt which was treated with 2,4-dichlorophenylhydrazine hydrochloride to give the pyrazole ester 12 (Murray and Wachter, 1989). Base hydrolysis (KOH/MeOH) of 12 furnished the corresponding acid which via its acid chloride was converted to the amide 13 using the same procedure as in the conversion of 6 to 7. Bromination ($Br_2$/AcOH) of 13 furnished 14 (O-1691) which on treatment with n-BuLi/n-$Bu_3$SnCl formed 15. The tin derivative 15 was then converted to the iodo analog 16 (O-1704) using the standard procedure.

Figure 5:
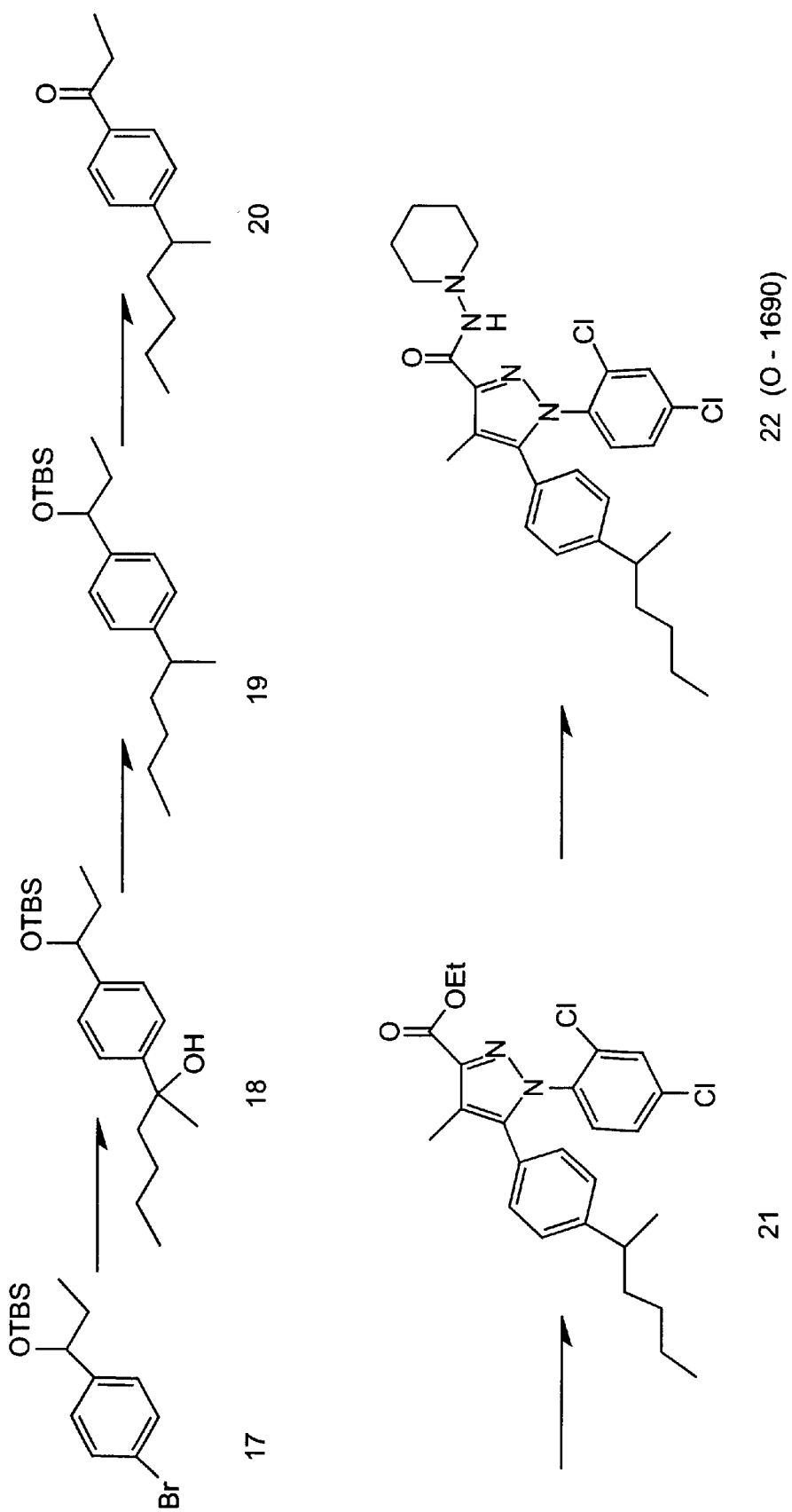
FIG. 5. Synthesis scheme 4.

The antagonist 22 (O-1690) was similarly synthesized from the ketone 20 in Scheme 4 (FIG. 5). However, the synthesis of 20 was achieved in a three step sequence from 17 which was formed by the reduction (NaBH$_4$/MeOH) of 4'-bromopropiophenone followed by hydroxyl group protection as the tertiarybutylsilyl (TBS) derivative. Treatment of 17 with n-BuLi/2-hexanone furnished the alcohol 18 which on treatment with Et$_3$SiH/BF$_3$.Et$_2$O/CH$_2$Cl$_2$ formed 19. Deprotection (tetrabutylammonium-fluoride, TBAF), followed by oxidation [N-methylmorpholine N-oxide (NMO)/tetrapropylammonium perruthenate (TPAP)] in CH$_2$Cl$_2$ furnished the ketone 20 (Griffith et al., 1987).

Experimental Section

All reagents were of commercial quality, reagent grade, and used without further purification. Anhydrous solvents were purchased from Aldrich and used without further purification. All reactions were carried out under a N2 atmosphere. Organic solutions were dried with sodium sulfate. $^1$H NMR spectra were recorded on either a Bruker 100 MHz, or a JEOL Eclipse 300 MHz spectrophotometer using CDCl$_3$ as the solvent with tetramethylsilane as an internal standard. Thin-layer chromatography (TLC) was carried out on Baker Si 250F plates and was developed upon treatment with phosphomolybdic acid (PMA). Flash column chromatography was carried out on EM Science silica gel 60. Elemental analyses were performed by Atlantic Microlab, Inc., Atlanta, Ga., and were found to be within +0.4% of calculated values for the elements shown, unless otherwise noted. All solutions were dried using anhydrous Na$_2$SO$_4$.

N-Methoxy-N-methyl-4-pentylbenzamide (2)

To a solution of 4-pentylbenzoic acid (5 g, 0.026 mol) in 260 ml of CH$_2$Cl$_2$ containing molecular sieves (4 Å), two drops of DMF was added, and then oxalyl chloride (5.45 g, 0.043 mol) was added dropwise. After stirring for 4.5 h the mixture was filtered, concentrated on the rotatory evaporator and pumped for 15 min. The residue was redissolved in 130 ml of CH$_2$Cl$_2$ and N,O-dimethylhydroxylamine HCl (3.04 g, 0.031 mol) was added at room temperature. After cooling the solution to 0° C., 5.3 ml of pyridine (0.065 mol) was added and the solution was stirred at 23° C. for 18 h. The solution was concentrated on the rotatory evaporator and the residue was partitioned between brine and a mixture of ether and CH$_2$Cl$_2$ (1:1). The organic layer was separated, dried and concentrated to yield 5.9 g (98%) of 2, which was used without further purification in the subsequent step. $^1$H NMR (100 MHz, CDCl3) δ 0.9 (t, 3H), 1.45 (m, 6H), 2.6 (t, J=6.4 Hz, 2H), 3.3 (s, 3H), 3.5 (s, 3H), 7.2 (d, J=8.0 Hz, 2H), 7.6 (d, J=8.2 Hz, 2H).

4-Pentylpropiophenone (3)

To a solution of the amide 2 (5.9 g, 0.025 mol) in 125 ml of dry THF, 63 ml of a 1.0 M THF solution of C$_2$H$_5$MgBr (0.063 mol) was added at 0° C. and then warmed to 23° C. after 20 min and continued stirring for an additional 1.5 h. The reaction was then quenched by the addition of sat NH$_4$Cl solution and extracted with hexanes. After the solution was concentrated on the rotatory evaporator, the residue was purified by flash chromatography, eluting with 2%–3% EtOAc/hexane mixtures to give 5.05 g (98%) of the ketone 3. $^1$H NMR (100 MHz, CDCl3) δ 0.9 (t, 3H), 1.4 (m, 9H), 2.6 (t, J=6.5 Hz, 2H), 2.95 (q, 2H), 7.2 (d, J=8.0 Hz, 2H), 7.9 (d, J=8.2 Hz, 2H).

4-Pentyl-2-bromopropiophenone (4)

To a solution of the ketone 3 (5.03 g, 0.025 mol) in 15 ml of glacial acetic acid, Br$_2$ (3.94 g, 0.025 mol) was added dropwise, with stirring at 0° C. After the addition was complete the ice bath was removed and the solution was stirred for 2 h at 23° C. The reaction mixture was quenched by the addition of water and after cooling it was extracted with ether. After drying and concentration under vacuum, the residue was purified by flash chromatography, eluting with hexanes, to afford 5.0 g (72%) of compound 4. $^1$H NMR (100 MHz, CDCl$_3$) δ 0.8 (t, 3H), 1.4 (m, 6H), 1.8 (d, J=6.5 Hz, 3H), 2.7 (t, J=6.4 Hz, 2H), 5.25 (q, 1H), 7.25 (d, J=8.0 Hz, 2H), 7.9 (d, J=8.2 Hz, 2H).

Ethyl[2-acetyl-3-methyl-4-(4-pentylphenyl)-4-oxo]butyrate (5)

To a suspension of NaH (1.185 g, 0.0296 mol; 60% in oil) in 53 ml of dry THF, ethylacetoacetate (3.28 g, 0.025 mol) was added dropwise with stirring at 0° C. The ice bath was then removed and after stirring for 0.5 h at 23° C. a solution of the bromoketone 4 (4.95 g, 0.017 mol) in 10 ml of dry THF was added portionwise. After stirring at 23° C. for 0.5 h, the mixture was refluxed for 1.5 h. After cooling, excess NaH was decomposed by the addition of water and the THF was removed on the rotatory evaporator. The residue was treated with an ether/water mixture and after separating, the ether layer was washed with water, dried, and evaporated. The residue was purified by flash chromatography, eluting with hexanes to 10% EtOAc/hexanes to afford 5 as an oil (3.12 g; 54%). $^1$H NMR (100 MHz, CDCl$_3$) δ 0.8 (t, 3H),1.2 (m, 12H), 2.35, 2.25 (s, 3H), 2.65 (m, 2H), 4.2 (m, 4H), 7.25 (d, J=8.0 Hz, 2H), 7.9 (d, J=8.2 Hz, 2H).

1-(2,4-Dichlorophenyl)-4-(methyl)-5-(pentylphenyl)-1H-pyrazole-3-carboxylic acid (6)

To a solution of sodium (0.187 g, 0.008 mol) in 20 ml of absolute ethanol, 2.0 g (0.006 mol) of the ester 5 dissolved in 2 ml of absolute alcohol was added. After stirring for 0.5 h at 23° C. the solution was cooled to 0° C. (ice bath). To this cold solution, with stirring, was added a solution of 2,4-dichlorodiazonium chloride solution (prepared from aniline (1.193 g, 0.0072 mol) in 3 ml of 24% HCl and diazotized (0–5° C.) with the slow addition of a solution of 0.52 g (0.0075 mol) of NaNO$_2$ in 3.5 ml of water) in five portions. After stirring for 2.5 h at 0° C., 115 ml of water was added to the mixture which was allowed to stand in the refrigerator for 16 h. The aqueous layer, was decanted and the residual red gum was dissolved in 40 ml of ethanol and 0.67 g of NaOH, dissolved in 3 ml of water, was added. After refluxing for 2 h, the alcohol was evaporated and to the dark residue added 150 ml of water and acidified with 6 N HCl. The mixture was extracted with EtOAc and the organic layer was washed with water, dried and evaporated to leave a gum which was purified by flash chromatography eluting with 20% EtOAc/hexane+2% acetic acid to afford 0.81 g (32%) of the acid 6 which was used as such in subsequent reactions.

N-(Piperidin-1-yl)-1-(2,4-dichlorophenyl)-4-methyl-5-(4-pentylphenyl)-1H-pyrazole-3-carboxamide (7); (O-1302)

To a solution of the acid 6 (0.3 g, 0.72 mmol) in 15 ml of dry CH$_2$Cl$_2$ (4 Å, molecular sieves), a drop of DMF was added, followed by the dropwise addition of oxaly chloride (0.15 ml, 1.19 mmol) with stirring. After 2.5 h the solution was evaporated on the rotatory evaporator. The acid chloride thus formed was dissolved in 8 ml of dry CH$_2$Cl$_2$ and triethylamine (0.15 ml, 1.1 mmol) was added followed by 1-aminopiperidine (0.10 ml, 0.94 mmol). The solution was stirred for 2 h at 23° C. after which it was washed with water/brine, dried and evaporated to leave a residue. It was purified by flash chromatography, eluting with 5%–30% EtOAc/hexane, to give 0.29 g (82%) of the amide 7. $^1$H NMR (100 MHz, CDCl3) δ 0.8 (t, 3H), 1.5 (m, 12H), 2.3 (s, 3H), 2.5 (m, 2H), 2.85 (t, J=5.0 Hz, 4H), 7.0 (m, 5H), 7.2 (brs, 1H), 7.4 (d, J=1.2 Hz, 1l), 7.6 (brs, 1H); Anal. Calcd. for C$_{27}$H$_{32}$Cl$_2$N$_4$O: C, 64.93; H, 6.46; N, 11.22. Found: C, 65.01; H, 6.47; N, 11.08; HRMS (Cl) calcd. (MH$^+$) 499.2031, found 499.2024.

5-(4-chlorophenyl)-1-(2,4-dichlorophenyl)-4-methyl-1H-pyrazole-3-carboxylic acid (9)

It was synthesized from 4'-chloropropiophenone using our previously described procedure (Dutta et al., 1995).

N-(n-pentyl)-5-(4-chlorophenyl)-1-(2,4-dichlorophenyl)-4-methyl-1H-pyrazole-3-carboxamide (10a); (O-1269)

The acid 9 (0.23 g, 0.6 mmol) was converted to its acid chloride and then treated with triethylamine (0.13 ml, 0.9 mmol) and n-pentylamine (0.09 ml, 0.78 mmol) in exactly the same manner as described above in the preparation of 7. It was purified by flash chromatography, eluting with 5%–30% EtOAc/hexane, to yield 0.11 g (39%) of 10a. $^1$H NMR (100 MHz, CDCl$_3$) δ 0.8 (t, 3H), 1.45 (m, 6H), 2.35 (s, 3H), 3.4 (q, 2H), 7.2 (m, 8H); Anal. Calcd for C$_{22}$H$_{22}$Cl$_3$N$_3$O: C, 58.62; H, 4.92; N, 9.32. Found: C, 58.47; H, 5.03; N, 9.16. HRMS (Cl) calcd. (MH$^+$) 450.0906, found 450.0923.

N-(n-heptyl)-5-(4-chlorophenyl)-1-(2,4-dichlorophenyl)-4-methyl-1H-pyrazole-3-carboxamide (10b); (O-1270)

It was synthesized as described for 10a except using n-heptylamine in place of n-pentylamine; (54%). $^1$H NMR (100 MHz, CDCl$_3$) δ 0.8(t, 3H), 1.4 (m, 10H), 2.3 (s, 3H), 3.4 q, 2H), 7.2 (m, 8H). Anal. Calcd. for C$_{24}$H$_{26}$Cl$_3$N$_3$O: C, 60.24; H, 5.47; N, 8.78. Found: C, 59.95; H, 5.58; N, 8.61. HRMS (Cl) calcd. (MH$^+$) 478.1220, found 478.1180.

N-(2-fluoroethyl)-5-(4-chlorophenyl)-1-(2,4-dichlorophenyl)-4-methyl-1H-pyrazol-3-carboxamide (10c); (O-1398)

It was synthesized as described for 10a using 2-fluoroethylamine; (63%). $^1$H NMR (300 MHz, CDCl$_3$) δ 2.3 (s, 3H), 3.7 (q, J=10.7, 4.9 Hz, 1 H), 3.8 (q J=10.7, 4.9 Hz, 1H), 4.5 (t, J=4.9 Hz, 1H), 4.66 (t, J=4.9 Hz, 1H) 7.05 (dt, J=6.8, 1.9 Hz, 2H), 7.28 (m, 5H), 7.4 (d, J=1.9 Hz, 1H). Anal. Calcd. for C$_{19}$H$_{15}$Cl$_3$N$_3$OF.0.1C$_6$H$_{14}$: C, 54.02; H 3.79; N, 9.65. Found: C, 54.11; H, 3.79; N, 9.51.

N-(n-propyl)-5-(4-chlorophenyl)-1-(2,4-dichlorophenyl)-4-methyl-1H-pyrazole-3-carboxamide (10d); (O-1399)

It was synthesized as described for 10a using propylamine; (69%). $^1$H NMR (300 MHz, CDCl$_3$)δ 1.0 (t, J=7.1 Hz, 3H), 1.6 (q, J=14.3, 7.2 Hz, 2H), 2.4 (s, 3H), 3.4 (q, J=14.0, 6.3 Hz, 2H), 6.95 (brs, 1H), 7.06 (d, J=6.6 Hz, 2H), 7.28 (m, 4H), 7.4 (d, J=1.9 Hz, 1H). Anal. Calcd. for C$_{20}$H$_{18}$Cl$_3$N$_3$O.0.1C$_6$H$_{14}$: C, 57.36; H, 4.53; N, 9.74. Found: C, 57.45; H, 4.57; N, 9.58.

4-Pentylacetophenone (11)

To a solution of 9-BBN (0.5 M in THF) (90.0 ml, 45.0 mmol) at 23° C., 1-pentene (4.93 ml, 45.0 mmol) was added. After 12 h, the solution was diluted with anhydrous dioxane (150 ml) and then 4-bromoacetophenone (5.97 g, 30.0 mmol) K$_3$PO$_4$ (9.55 g, 45.0 mmol), Pd(PPh$_3$)$_4$ (0.867 g, 0.750 mmol) were added. After deoxygenating the solution with N$_2$ for 20 min, the solution was refluxed for 12 h. After cooling to ambient temperature, 3N NaOH (40 ml) and 30% H$_2$O$_2$ (40 ml) were added dropwise followed by dilution with hexanes (200 ml). After separation of layers, the organic layer was washed with brine (200 ml), dried, and concentrated under reduced pressure. The crude product was purified by flash chromatography eluting with 10% EtOAc/hexanes, to afford 4.09 g of 11 as an oil (72%). $^1$H NMR (CDCl$_3$) δ 0.88 (t, J=6.9 Hz, 3H), 1.23–1.36 (m, 4H), 1.55–1.69 (m, 2H), 2.58 (s, 3 H), 2.66 (t, J=7.7 Hz, 2H), 7.25 (d, J=1.9 Hz, 2H), 7.86 (d, J=1.9 Hz, 2H); $^{13}$C NMR (CDCl3) δ 14.09, 22.58, 26.65, 30.89, 31.51, 36.04, 128.55, 128.68, 134.97, 148.92, 197.98.

Ethyl-3-(2,4-dichlorophenyl)-4-(4'-n-pentylphenyl) pyrazole carboxylate (12)

To a solution of LiHMDS (1M, 15.5 ml, 15.5 mmol) in anhydrous Et2O (78.0 ml) at 78° C., a solution of 4-pentylacetophenone (2.94 g, 15.5 mmol) in anhydrous Et2O (19 ml) was added. After 45 min, diethyl oxalate (2.32 ml, 17.05 mmol) was added and then the solution was allowed to slowly warm to 23° C. After another 16 h at 23° C., the solution was diluted with pentane (30 ml) and the precipitated solid was collected by filtration. The solid was rinsed with excess pentane and then dried under high vacuum. $^1$H NMR (CDCl$_3$) δ 0.89 (t, J=6.6 Hz, 3H), 1.01 (t, J=6.9 Hz, 3H), 1.25–1.34 (m, 4H), 1.56–1.67 (m, 2H), 2.64 (t, J=7.4 Hz, 2H), 3.87–3.89 (m, 2H), 6.58 (s, 1H), 7.20 (d, J=7.9 Hz, 2H), 7.85 (d, J=7.9 Hz, 2H). To a solution of the lithium enolate (1.48 g, 5.0 mmol) in EtOH (17.0 ml) at 23° C. was added 2,4-dichirophenylhydrazine hydrochloride (1.17 g, 5.5 mmol). After 20 h, the solution was concentrated under reduced pressure. The resulting residue was redissolved in AcOH (12.5 ml) and heated under reflux for 24 h. After cooling to ambient temperature, the reaction mixture was poured into ice water (30 ml) and extracted 3× with EtOAc (30 ml). The combined organic layers were washed with H$_2$O (60 ml), saturated NaHCO$_3$ (60 ml), brine (60 ml), dried, and concentrated under reduced pressure. The crude product was purified by flash chromatography eluting with 20% EtOAc/hexanes, to afford 1.85 g of 12 (86%). $^1$H NMR (CDCl$_3$) δ 0.87 (t, J=6.9 Hz, 3H), 1.25–0.143 (m, 4H), 1.52–1.61 (m, 2H), 2.56 (t, J=7.7 Hz, 2H), 4.43 (q, J=7.2 Hz, 2H), 6.58 (s, 1H), 7.08–7.43 (m, 4H).

N-(N-Piperdyl)-3-(2,4-dichlrophenyl)-4-(4'-pentylphenyl)pyrazole carboxamide (13)

To a solution of ethyl-3-(2,4-dichlorophenyl)-4-(4'-n-pentylphenyl)pyrazole carboxylate (1.98 g, 4.59 mmol) in MeOH (12.0 ml), a solution of KOH 0.515 g, (9.18 mmol) in (12.0 ml) MeOH was added, then the solution was refluxed for 3 h. After cooling to ambient temperature, the solution was poured into H2O (25 ml) and acidified to pH~3 with 3 M HCl and then the solution was extracted 2× with CH2Cl2 (25 ml). The combined organic layers were dried, and concentrated under reduced pressure. To a solution of the crude acid in anhydrous CH$_2$Cl$_2$ (18.0 ml) was added oxalyl chloride (0.440 ml, 5.05 mmol) plus one drop of DMF. The solution was refluxed for 1 h and then concentrated under reduced pressure. To a solution of the acid chloride in CH$_2$Cl$_2$ (18.0 ml) at 0° C. was added Et$_3$N (1.92 ml, 13.77 mmol), 1-aminopiperdine (0.743 ml, 6.89 mmol). After 4 h, the solution was diluted with CH$_2$Cl$_2$ (20 ml) washed with water, saturated NaHCO$_3$, dried and concentrated under reduced pressure. The crude product was purified by flash chromatography eluting with 50% EtOAc/hexanes, followed by crystallization with EtOAc/hexanes to afford 1.74 g of 13 as a white solid (78%). $^1$H NMR (CDCl$_3$) δ 0.87 (t, J=6.6 Hz, 3H), 1.24–1.39 (m, 4H), 1.42–1.48 (m, 2H), 1.50–1.61 (m, 2H), 1.73–1.80 (m, 4H), 2.55 (t, J=7.7 Hz, 2H), 2.83–2.87 (m, 4H), 7.06–7.58 (m, 9 H); $^{13}$C NMR (CDCl$_3$) δ 14.08, 22.55, 23.39, 23.36, 30.86, 31.56, 35.70, 57.32, 107.23, 127.84, 127.96, 128.05, 128.78, 128.91, 130.50, 130.65, 133.29, 136.08, 144.03, 146.90, 147.54, 158.97. Anal. Calcd for C$_{26}$H$_3$ON$_4$OCl$_2$: C, 64.33; H, 6.23; N, 11.54. Found: C, 64.35; H, 6.29; N, 11.37.

N-(N-Piperdyl)-3-(2,4-dichlrophenyl)-4-(4'-pentylphenyl)-5-bromopyrazole-carboxamide (14); (O-1691)

To a solution of N-(N-piperdyl)-3-(2,4-dichlrophenyl)-4-(4'-pentylphenyl) pyrazole carboxamide (1.99 g, 4.10 mmol) in AcOH (20.5 ml) at 23° C., Br$_2$ (1.06 ml, 20.5 mmol) was added dropwise. After 15 min., the reaction was quenched with saturated Na$_2$SO$_3$ (10 ml) and diluted with ether (80 ml). After separation of layers, the organic layer was washed with saturated Na$_2$SO$_3$, H$_2$O (15 ml), saturated NaHCO$_3$ (15 ml), brine (15 ml), dried, and concentrated under reduced pressure. The crude product was purified by flash chromatography eluting with 10% EtOAc/hexanes, to afford 1.20 g of 14 (52%). $^1$H NMR (Acetone-d6) δ 0.86 (t, J=6.9 Hz, 3H), 1.22–1.47 (m, 6H), 1.52–1.69 (m, 6H), 2.59 (t, J=7.7 Hz, 2H), 2.89–2.93 (m, 4H), 7.20–7.29 (m, 4H), 7.51–7.77 (m, 3H), 8.36 (s, 1H); $^{13}$C NMR (CDCl$_3$) δ 14.08, 22.55, 23.41, 25.50, 30.72, 31.61, 35.81, 56.92, 95.62, 124.33, 127.92, 128.58, 129.55, 130.39, 130.58, 133.11, 135.93, 136.34, 143.36, 144.68, 145.16, 158.21. Anal Calcd for C26H29N4OCl2Br: C, 55.34; H, 5.18; N, 9.93. Found: C, 55.27; H, 5.24; N, 9.86.

N-(N-Piperdyl)-3-(2,4-dichlrophenyl)-4-(4'-pentylphenyl)-5-tri-n-butylstannylpyrazole carboxamide (15)

To a solution of N-(N-piperdyl)-3-(2,4-dichlrophenyl)-4-(4'-pentylphenyl)-5-bromopyrazole carboxamide (0.867 g, 1.54 mmol) in anhydrous THF (7.7 ml) at 78° C., a solution of n-BuLi (1.54 ml, 3.84 mmol) in hexanes was added dropwise. After 30 min, n-Bu$_3$SnCl (1.25 ml, 4.62 mmol) was added and allowed the reaction to slowly warm to 23° C. After another 2 h, the reaction was diluted with Et$_2$O (15 ml) and quenched with H$_2$O (10 ml). After separation of layers, the organic layer was washed with 1 M NaOH 2× (10 ml), brine (10 ml), dried, and concentrated under reduced pressure. The crude product was purified by radial chromatography eluting with 10% EtOAc/hexanes, to afford 0.528 g of 15 as an oil (44%). $^1$H NMR (CDCl$_3$) δ 0.72–0.98 (m, 18H), 1.08–1.77 (m, 24H), 2.51–2.57 (m, 2H), 2.81–2.89 (m, 4H), 7.01–7.55 (m, 8H); $^{13}$C NMR (CDCl$_3$) δ 10.87, 13.79, 14.05, 22.57, 22.73, 25.29, 27.36, 29.20, 31.53, 31.67, 35.74, 57.58, 114.76, 127.63, 127.81, 127.91, 128.06, 128.42, 129.95, 130.12, 130.74, 133.72, 135.81, 136.46, 143.79, 160.28. Anal. Calcd for C$_{38}$H$_{56}$N$_4$OCl$_2$Sn: C, 58.94; H, 7.29; N, 7.23. Found: C, 59.05; H, 7.30; N, 7.11.

N-(N-Piperdyl)-3-(2,4-dichlrophenyl)-4-(4"-pentylphenyl)-5-iodopyrazole-carboxamide (16); (O-1704)

To a solution of N-(N-piperdyl)-3-(2,4-dichlrophenyl)-4-(4"-pentylphenyl)-5-tri-n-butylstannylpyrazole carboxamide (0.100 g, 0.129 mmol) in CHCl$_3$ (1.30 ml) at 23° C., 12 (0.036 g, 0.142 mmol) was added. After 30 min, the reaction was quenched with saturated Na$_2$SO$_3$ (2 ml), diluted with CH$_2$Cl$_2$ (7 ml) and made basic pH~10 with 1 M NaOH. After separation of layers, the organic layer was dried, and concentrated under reduced pressure. The crude product was purified by radical chromatography eluting with 20% EtOAc/hexanes, to afford 0.069 g 16 as a foam (87%). $^1$H NMR (CDCl$_3$) δ 0.87 (t, J=6.8 Hz, 3H), 1.20–1.85 (m, 12H), 2.56 (t, J=7.7 Hz, 2H), 2.82–2.95 (m, 4H), 7.10–7.32 (m, 6H), 7.41 (s, 1H), 7.62 (s, 1H), $^{13}$C NMR (CDCl$_3$) δ 14.08, 22.65, 23.42, 25.54, 30.68, 31.63, 35.80, 56.92, 61.84, 126.10, 127.82, 128.49, 129.92, 130.34, 130.54, 133.12, 136.07, 136.27, 144.64, 145.27, 148.59, 158.44. Anal. Calcd for C$_{26}$ H$_{29}$N$_4$OCl$_2$I: C, 58.94; H, 7.29; N, 7.23. Found: C, 59.05; H, 7.30; N, 7.11.

4-Bromo-1-(1'-O-t-butyldimethylsilylhydroxy) propylbenzene (17)

To a solution of 4-bromopropiophenone (10.7 g, 50.0 mmol) in MeOH (100 ml) at 0° C., NaBH$_4$ (2.08 g, 55.0 mmol) was added in portions. After 1 h, the solution was diluted with Et$_2$O (150 ml) and made acidic (pH~4) with 1 M HCl. After separation of layers, the organic layer was washed with H$_2$O (75 ml), brine (75 ml), dried and concentrated under reduced pressure. To a solution of the alcohol and imidazole (10.2 g, 150 mmol) in anhydrous CH$_2$Cl$_2$ (50.0 ml) at 23° C. was added TBSCI (11.3 g, 75.0 mmol). After 12 h, the solution was diluted with ether (150 ml), washed with cold 1 M HCl (75 ml), saturated NaHCO$_3$ (75 ml), dried and concentrated under reduced pressure. The crude product was purified by flash chromatography eluting with 5% EtOAc/hexanes, to afford 16.2 g of 17 as an oil (98%). $^1$H NMR (CDCl$_3$) δ −0.13 (s, 3H), 0.02 (s, 3H), 0.81 (t, J=7.4 Hz, 3H), 0.88 (s, 9H), 4.51–4.55 (m, 1H), 7.15–7.43 (m, 4H); $^{13}$C NMR (CDCl$_3$) δ −4.89, −4.59, 9.88, 18.29, 25.90, 33.68, 75.63, 120.47, 127.72, 131.12, 144.81.

4-(1'-Hydroxy-1'-methylpentyl)-1-(1'-O-t-butyldimethylsilylhydroxy)propyl-benzene (18)

To a solution of 17 (12.7 g, 38.6 mmol) in THF (129 ml) at 78° C., a solution of n-BuLi in hexanes (17.0 ml, 42.5 mmol) was added. After 30 min, 2-hexanone (7.14 ml, 57.9 mmol) was added dropwise, then the solution was allowed to slowly warm to 23° C. After 8 h, the solution was diluted with Et$_2$O (150 ml) and slowly made acidic (pH~4) with 1 M HCl. After separation of layers, the organic layer was washed with brine, dried and concentrated under reduced pressure. The crude product was purified by flash chromatography eluting with 10% EtOAc/hexanes, to afford 10.9 g of 18 as an oil (81%). $^1$H NMR (CDCl$_3$) δ −0.15 (s, 3H), 0.00 (s, 3H), 0.80–1.04 (m, 3H), 0.87 (s, 9H), 1.06–1.28 (m, 4H), 1.54 (s, 3H), 1.62–1.81 (m, 4H), 4.53–4.57 (m, 4H), 7.25–7.35 (m, 4H).

4-(1'-Methylpentyl)-1-(1'-O-t-butyldimethylsilylhydroxy)propylbenzene (19)

To a solution of 18 (8.23 g, 23.5 mmol) and Et$_3$SiH (4.50 ml, 28.2 mmol) in anhydrous CH$_2$Cl$_2$ (94.0 ml) at 78° C., BF$_3$Et$_2$O (6.55 ml, 51.7 mmol) was added dropwise. After 4 h, the solution was quenched with MeOH (15 ml), warmed to 0° C. and then added sat NaHCO$_3$ (100 ml). After separation of layers, the organic layer was dried, and concentrated under reduced pressure. The crude product was purified by flash chromatography eluting with 5% EtOAc/hexanes, to afford 5.72 g of 19 as an oil (73%). $^1$H NMR (CDCl$_3$) δ −0.15 (s, 3H), 0.00 (s, 3H), 0.80 (t, J=7.2 Hz, 3H), 0.85 (s, 9H), 1.20 (d, J=6.9 Hz, 3H), 1.35–1.67 (m, 11H), 2.59–2.67 (m, 1H), 4.51–4.53 (m, 1H), 7.22–7.64 (m, 4H); $^{13}$C NMR (CDCl$_3$) δ −4.86, −4.58, 10.19, 14.15, 22.29, 22.83, 25.96, 30.01, 33.68, 38.34, 39.62, 125.87, 126.50, 142.55, 146.58.

4-(1'-methylpentyl)propiophenone (20)

To a solution of 19 (2.75 g, 8.24 mmol) in anhydrous THF (27.5 ml) at 23° C., a solution of TBAF (12.4 ml, 12.4 mmol) was added. After 2 h, the reaction mixture was diluted with Et$_2$O (30 ml), washed with H2O (30 ml), brine (30 ml), dried, and concentrated under reduced pressure. To a mixture of the alcohol, NMO (1.45 g, 12.4 mmol), and 4 Å molecular sieves (6.6 g) in CH$_2$Cl$_2$ (42.0 ml), TPAP (0.145 g, 0.412 mmol) was added at 23° C. After 2 h, the solution was filtered through a plug silica and celite and concentrated under reduced pressure. The crude product was purified by radical chromatography eluting with 5% EtOAc/hexanes, to afford 1.78 g of 20 as an oil (99%). $^1$H NMR (CDCl$_3$) δ 0.83 (t, J=7.2 Hz, 3H), 1.08–1.28 (m, 7H), 1.20 (d, J=6.9 Hz, 3H), 1.56–1.62 (m, 2H), 2.69–2.74 (m, 1H), 2.96 (q, J=7.2 Hz, 2H), 7.25 (d, J=8.3 Hz, 2H), 7.89 (d, J=8.0 Hz, 2H); $^{13}$C NMR (CDCl$_3$) δ 8.42, 14.07, 22.13, 22.78, 29.92, 31.73, 37.93, 40.12, 127.26, 128.26, 129.41, 135.06, 153.80, 200.99.

Ethyl-3-(2,4-dichlrophenyl)-4-(4'-(1'-methylpentyl)phenyl)-5-methylpyrazole carboxylate (21)

To a solution of LiHMDS (1M, 7.79 ml, 7.79 mmol) in anhydrous Et$_2$O (20.0 ml) at 78° C., a solution of the ketone 20 (1.70 g, 7.79 mmol) in anhydrous Et$_2$O (19 ml) was added. After 45 min, diethyl oxalate (1.16 ml, 8.57 mmol) was added and the solution was then allowed to slowly warm to 23° C. After another 16 h at 23° C., the solution was diluted with pentane (30 ml) and the precipitated solid was collected by filtration. The solid was rinsed with excess pentane and then dried under high vacuum. To a solution of the enolate (1.70 g, 7.79 mmol) in EtOH (26.0 ml) at 23° C. was added 2,4-dichirophenylhydrazine hydrochloride (1.83 g, 8.57 mmol). After 20 h, the solution was concentrated under reduced pressure. The resulting residue was redissolved in AcOH (19.0 ml) and heated under reflux for 24 h. After cooling to ambient temperature, the reaction mixture was poured into ice water (30 ml) and extracted 3× with EtOAc (30 ml). The combined organic layers were washed with H2O (60 ml), saturated NaHCO$_3$ (60 ml), brine (60 ml), dried and concentrated under reduced pressure. The crude product was purified by flash chromatography eluting with 20% EtOAc/hexanes, to afford 0.909 g of 21 (25%). $^1$H NMR (CDCl$_3$) δ 0.85 (t, J=7.2 Hz, 3H), 1.17 (d, J=6.9 Hz, 3H), 1.21 (d, J=6.9 Hz, 3H), 1.20–1.26 (m, 4H), 1.40 (t, J=7.2 Hz, 3H), 1.47–1.52 (m, 2H), 2.34 (s, 3H), 2.59–2.64 (m, 1H), 4.43 (q, J=7.2 Hz, 2H), 7.01–7.36 (m, 7H); $^{13}$C NMR (CDCl$_3$) δ 9.99, 14.02, 14.55, 21.90, 22.75, 29.91, 38.06, 39.71, 60.95, 118.82, 125.94, 127.16, 127.58, 129.53, 130.01, 133.35, 135.69, 142.90, 144.27, 148.78, 163.09.

N-(N-Piperdyl)-3-(2,4-dichlrophenyl)-4-(4'-(1'-methylpentyl)phenyl)-5-methylpyrazole carboxamide (22); (O-1690)

To a solution of 21 (0.771 g, 1.68 mmol) in MeOH (4.2 ml), a solution of KOH in 4.2 ml of MeOH was added, and the solution was refluxed for 3 h. After cooling to ambient temperature, the solution was poured into H$_2$O (8.0 ml) and acidified to pH≈3 with 3 M HCl and then the solution was extracted 2× with CH2Cl2 (10 ml). The combined organic layers were dried and concentrated under reduced pressure. To a solution of the crude acid in anhydrous CH$_2$Cl$_2$ (6.7 ml) was added oxalyl chloride (0.161 ml) plus one drop of DMF. The solution was refluxed for 1 h, then concentrated under reduced pressure. To a solution of the acid chloride in CH$_2$Cl$_2$ (6.7 ml) at 0° C. was added Et3N (0.702 ml, 5.04 mmol), 1-aminopiperdine (0.272 ml, 2.52 mmol) and DMAP (0.013 g, 0.084 mmol). After 2 h, the solution was diluted with CH$_2$Cl$_2$ (10 ml) and the organic layer was washed with water, saturated NaHCO$_3$, dried and concentrated under reduced pressure. The crude product was purified by flash chromatography eluting with 10% EtOAc/hexanes, to afford 0.562 g of 22 as a white foam (65%). $^1$H NMR (CDCl$_3$) δ 0.82 (t, J=7.4 Hz, 3H), 1.17 (d, J=6.9 Hz, 3H), 1.20–1.51 (m, 8H), 1.72–1.74 (m, 4H), 2.37 (s, 3H), 2.58–2.63 (m, 1H), 2.83–2.87 (m, 4H), 6.98–7.63 (m, 8H); 13C NMR (CDCl$_3$) δ 9.53, 14.11, 21.91, 22.80, 23.50, 25.51, 29.93, 38.06, 39.71, 57.15, 117.85, 126.06, 127.70, 129.44, 130.74, 133.21, 135.61, 144.38, 148.68, 160.29; Anal. (C$_{28}$H$_{34}$N$_4$OCl$_2$.0.3C6H14) Calcd: C, 65.49; H, 6.67; N, 10.91. Found: C, 65.76; H, 6.78; N, 10.89.

EXAMPLE 2

Biological Activity

METHODS

Subjects:

Male ICR mice (25–32 g), purchased from Harlan (Dublin, Va.), were housed in groups of five. All animals were kept in a temperature-controlled (20–22° C.) environment with a 12-hour light-dark cycle (lights on at 7 a.m.). Separate mice were used for testing each drug dose in the in vivo behavioral procedures. The mice were maintained on a 14:10 hour light: dark cycle, and received food and water ad libitum. Brain tissue for binding studies was obtained from male Sprague-Dawley rats (150–200 g) purchased from Harlan Laboratories (Dublin, Va.).

Apparatus:

Measurement of spontaneous activity in mice occurred in standard activity chambers interfaced with a Digiscan Animal Activity Monitor (Omnitech Electronics, Inc., Columbus, Ohio). A standard tail-flick apparatus (described by Dewey et al., 1970) and a digital thermometer (Fisher Scientific, Pittsburgh, Pa.) were used to measure antinociception and rectal temperature, respectively.

Drugs:

$\Delta^9$-THC (National Institute on Drug Abuse, Rockville, Md.) and CP 55,940 (Pfizer, Groton, Conn.) were suspended in a vehicle of absolute ethanol, Emulphor-620 (Rhone-Poulenc, Inc., Princeton, N.J.), and saline in a ratio of 1:1:18. SR 141716A (National Institute on Drug Abuse) and novel pyrazole cannabinoids (synthesized in our labs), were also mixed in 1:1:18 vehicle. All drugs were administered to the mice intravenously (i.v.) in the tail vein at a volume of 0.1 ml/10 g.

Membrane Preparation and Binding:

The methods used for tissue preparation and binding have been described previously (Compton et al., 1993) and are similar to those described by Devane et al. (1988). All assays, as described briefly below, were performed in triplicate, and the results represent the combined data from three to six individual experiments. Following decapitation and rapid removal of the brain, whole brain was homogenized and centrifuged. The resulting pellet was termed P1. The supernatant was saved and combined with the two subsequent supernatants obtained from washing of the P1 pellet. The combined supernatant fractions were centrifuged, resulting in the P2 pellet. After further incubation and centrifuging, this pellet was resuspended in assay buffer to a protein concentration of approximately 2 mg/ml. The membrane preparation was quickly frozen in a bath solution of dry ice and 2-methylbutane (Sigma Chemical Co., St. Louis, Mo.), then stored at −80° C. for no more than 2 weeks. Prior to performing a binding assay an aliquot of frozen membrane was rapidly thawed and protein values determined by the method of Bradford (1976). Binding was initiated by the addition of 150 µg of P2 membrane to test tubes containing 1 nM of [3H] CP 55,940 (79 Ci/mmol) and a sufficient quantity of buffer to bring the total incubation volume to 1 ml. Nonspecific binding was determined by the addition of 1 µM unlabeled CP 55,940. Following incubation at 30° C. for 1 hr, binding was terminated by addition of ice-cold buffer and vacuum filtration through pretreated filters in a 12-well sampling manifold (Millipore, Bedford, Mass.). After washing, filters were placed into plastic scintillation vials (Packard, Downer Grove, Ill.) and shaken. The quantity of radioactivity present was determined by liquid scintillation spectrometry.

Procedure:

Prior to testing in the behavioral procedures, mice were acclimated to the experimental setting (ambient temperature 22–24° C.) overnight. Pre-injection control values were determined for rectal temperature and tail-flick latency (in sec). For agonism tests, mice were injected i.v. with drug or vehicle and, five min later, were placed in individual activity chambers where spontaneous activity was measured for 10 min. Activity was measured as total number of interruptions of 16 photocell beams per chamber during the 10-min test and was expressed as % inhibition of activity of the vehicle group. Tail-flick latency was measured at 20 min post-injection. Maximum latency of 10 sec was used. Antinociception was calculated as percent of maximum possible effect {%MPE=[(test−control latency)/(10−control)]×100}. Control latencies typically ranged from 1.5 to 4.0 sec. At 30 min post-injection, rectal temperature was measured. This value was expressed as the difference between control temperature (before injection) and temperatures following drug administration($\Delta$° C.). Different mice (n=5–6) were tested for each dose of each compound. Each mouse was tested in each of the 3 procedures. Antagonism tests were conducted using an identical procedure with the exception that the antagonist analog was injected 10 min prior to the injection of 3 mg/kg $\Delta^9$-THC.

Data Analysis:

Based on data obtained from numerous previous studies with cannabinoids, maximal cannabinoid effects in each procedure were estimated as follows: 90% inhibition of spontaneous activity, 100% MPE in the tail flick procedure, and −6° C. change in rectal temperature. $ED_{50}$'s were defined as the dose at which half maximal effect occurred. For drugs that produced one or more cannabinoid effect, $ED_{50}$'s were calculated separately using least-squares linear regression on the linear part of the dose-effect curve for each in vivo measure, plotted against $\log_{10}$ transformation of the dose. For the purposes of potency comparison, potencies were expressed as µmol/kg. Data collected during combination tests (analog dose+3 mg/kg $\Delta^9$-THC) were converted to percent antagonism [(mean score of group that received vehicle and 3 mg/kg $\Delta^9$-THC-score obtained with analog dose and 3 mg/kg $\Delta^9$-THC)/(mean score of group that received vehicle and 3 mg/kg $\Delta^9$-THC)×100]. When the resulting values showed dose-responsiveness, $AD_{50}$'s were calculated separately using least-squares linear regression on the linear part of the % antagonism curve for each in vivo measure, plotted against $\log_{10}$ transformation of the dose. For the purposes of potency comparison, antagonist potencies were expressed as µmol/kg.

RESULTS

Binding Affinities:

Table 1 shows binding affinities for pyrazole analogs in which the carboxyamide group of the 3-substituent of SR141716A was replaced with an alkylether group. Substitution of an alkylether group for the carboxyamide group with retention of the terminal piperidine group, as in O-848, greatly decreased binding affinity for CB1 receptors. While affinity was improved (compared to O-848) by substitution of various cyclic, bicyclic, or tricyclic structures for the piperidine ring of O-848, most compounds listed in Table 1 still had relatively little affinity for the CB1 receptor (Ki>100 nM). Notable exceptions were O-852, O-889, and O-1043, each of which had CB1 affinity <100 nM. In addition to substitution of an alkylether for the carboxamide at position 3 on the pyrazole core (as with all compounds in this series), these compounds had substitutions of napthalene (O-852), 4-fluorophenyl (O-889), and 2,4-difluorophenyl (O-1043) groups for the piperidine of the parent compound, SR 141716A. Nevertheless, CB1 affinity of these three compounds were substantially less than that of SR 141716A.

Table 2 shows the binding affinities of compounds in which the n-piperidine at the 3-position of SR 141716A was replaced by a carbon chain that more directly corresponds to the lipophilic side chain of $\Delta^9$-THC. Some of these compounds retained the amide group at position 3 on the pyrazole core (O-1269, O-1270, O-1398, and O-1399) while others had a ketone substitution at this position (O-1271 and O-1272). Still others had substitutions of a heptyl chain without branching (O-1877) or with an attached 1' hydroxyl group (O-1876). In all cases, binding affinities were greatly enhanced compared to 3-substituent substitution with an alkylether group, as in O-848, but still were 5- to 137-fold less than SR 141716A. Of the compounds retaining the amide group, the n-pentyl compound, O-1269, had the greatest affinity. Affinity was only slightly decreased by substituting n-heptyl (O-1270), but was decreased 5-fold through n-propyl substitution (O-1399). Fluroethyl substitution (O-1398) produced a further 5-fold reduction in affinity. Replacement of the amide group with a ketone (O-1271 and O-1272) also resulted in decreased affinity compared to compounds with identical side chain lengths that retained the amide group (O-1269 and O-1270, respectively). In each of the pairs, the compound with n-pentyl substitution (O-1269 and O-1271) had the best affinity, suggesting that substituent length affected $CB_1$ receptor binding of both series.

In SR 141716A, a 2,4-dichlorophenyl group is attached to the pyrazole ring at position 1. Substitutions for this 1-substituent (Table 3) decreased $CB_1$ receptor binding affinities. Removal of the chlorines from the 2,4-dichlorophenyl group (O-1300) decreased affinity by 24-fold compared to SR 141716A. Removal of the chlorine at the 2-position of the 2,4-dichlorophenyl group and replacement of the chlorine at the 4-position with a n-butyl (O-1254) or n-pentyl (O-1255) chain further reduced affinity, with the n-pentyl compound having almost 2-fold less affinity than the n-butyl compound. In contrast, branching of the substituent at the para-position of the phenyl group at the 1-position of SR 141716A (i.e., substitution of a p-secbutyl group; O-1253) increased affinity compared to the non-branched chain analog O-1254. Nevertheless, none of the 1-substituent substitutions presented in Table 3 produced compounds with $CB_1$ receptor binding affinities that equaled that of SR 141716A. While the affinity of O-1253, the compound with the best affinity, was nearly equal to that of $\Delta^9$-THC, it was 8-fold less than that of SR 141716A.

Table 4 shows the affinities for analogs in which the 4- and/or 5-substituent were manipulated. Replacement of the p-chlorophenyl group at the 5-position of the pyrazole core with a branched carbon chain (1'-methylpentyl) resulted in the compound (O-1559) with the lowest binding affinity. Other compounds in this series retained the phenyl group of SR 141716A, but had methylated or nonmethylated pentyl substitution for the chloro at the para-position of the phenyl. N-pentyl substitution (O-1302) produced a compound with $CB_1$ receptor binding affinity approximately 3-fold greater than that of SR 141716A. Substitution of a 1'-methylpentyl chain (O-1690) did not substantially alter affinity nor did an iodine substitution for the methyl group at the 4-position of the pyrazole core (O-1704). An identical compound with a bromine substitution at the 4-position of the pyrazole only slightly increased affinity (O-1691) whereas a hydrogen substitution at this position produced a 12-fold decrease in affinity (O-1710).

Structure-Activity Relationship for Agonist Activity in Mice:

3-Substituent substitution of an alkylether group for the amide and various cyclic structures for the piperidine of SR141716A resulted in analogs that engendered slight in vivo cannabimimetic effects. Minor activity (30–70% of maximum effect) was observed with several compounds (Table 1). The most potent cannabimimetic activity in this series was produced by a compound (O-889) with a 3-substituent substitution of a p-fluorophenyl methoxy group. O-889 had full or partial activity in all three assays and also had one of the highest $CB_1$ receptor affinities in the series (Table 1). In addition, O-889 stimulated locomotor activity by about 30% at a dose lower than those that produced suppression of locomotor activity (Table 5). O-852 also stimulated locomotion by 52%, but unlike O-889, this compound did not inhibit locomotor activity at higher doses nor was it active in the antinociceptive or hypothermia assays.

In contrast, analogs in which a lipophilic carbon chain replaced the terminal piperidine of the 3-substituent of SR 141716A showed greater cannabimimetic activity (Table 2). Retention of the amide group with substitution of n-pentyl or n-heptyl for the terminal piperidine of SR 141716A (O-1269 and O-1270, respectively) resulted in agonist activity, whereas ketone substitution for the amide group with identical n-pentyl and n-heptyl substitutions for the piperidine (O-1271 and O-1272) eliminated in vivo cannabimimetic activity. Substitution of a non-branched heptyl chain or one with a 1'-hydroxyl group also resulted in inactive compounds. In contrast, in vivo potency in all three assays was maintained or even increased when the amide group of O-1269 was shortened from n-pentyl to n-propyl (O-1399) or to 2-fluoroethyl (O-1398). Unexpectedly, however, $CB_1$ binding affinity decreased 5- and 27-fold (O-1399 and O-1398, respectively) with these shortened chain lengths, representing a disparity between affinity and potency for these two compounds that is not easily explained. Of this series of analogs, only O-1270 and O-1271 stimulated locomotor activity to any notable extent (29% and 54%, respectively).

Tables 3 and 4 show the results of in vivo tests for analogs with various 1-substituent or 4- and 5-substituent substitutions, respectively. None of these compounds produced any of the characteristic effects of cannabinoid agonists in the triad of tests even though each was tested up to an i.v. dose of 30 mg/kg. Indeed, several of these compounds markedly enhanced locomotor activity (50–118%) rather than inhibiting it as do cannabinoid agonists (Table 5). For analogs with substituents at position 5, co-administration with 3 mg/kg $\Delta^9$-THC tended to increase the degree of stimulation. As a group, these stimulatory analogs had diverse structural substitutions. Further, their binding affinities ranged from 2.2 to 233 nM (O-1704 and O-1559, respectively), suggesting little correlation between $CB_1$ receptor affinity and potency for this effect.

In short, with the exception of analogs with carbon side chain substitution at position 3 of the pyrazole core, strong agonist activity was not observed for any of the compounds synthesized, at least at doses below 30 mg/kg (highest dose tested for any analog). A correlation between binding affinity and agonist potency was not calculated because too few analogs were active for such a correlation to be meaningful; however, visual inspection reveals that any correlation is likely to be low. For example, although O-1269 and O-1398 have similar $ED_{50}$'s in vivo, they have drastically different $K_i$ values. In addition, analogs presented in Table 4 have excellent binding affinities; yet, they are not agonists in any of the in vivo assays.

Structure-Activity Relationship for Antagonist Activity in Mice:

In order to assess antagonist activity, SR 141716A and its analogs from each series with good binding affinities (<100 nM) were tested in combination with an active dose of $\Delta^9$-THC (3 mg/kg, i.v.). The results of these tests are presented in Table 6. As expected, SR141716A fully antagonized the suppression of locomotor activity, antinociceptive, and hypothermic effects induced by 3 mg/kg $\Delta^9$-THC. Analogs with 3-substituent substitutions produced partial antagonism at best and often were ineffective. Maximum antagonist activity was obtained with O-1271 which produced an average of 59% antagonism across the three measures and did not have agonist properties at doses up to 30 mg/kg. With the exception of O-1253, 1-substituent substitution also did not result in marked antagonist activity. Interestingly, O-1253 also had the highest $CB_1$ binding affinity in this series of compounds. When tested in combination with 3 mg/kg $\Delta^9$-THC, O-1253 produced full, dose-dependent antagonism of the antinociceptive and hypothermic effects of this dose of $\Delta^9$-THC, but antagonized its locomotor suppressant effects only at a single dose (1 mg/kg) with stimulation at higher doses and no antagonism at lower doses.

Figure 6:
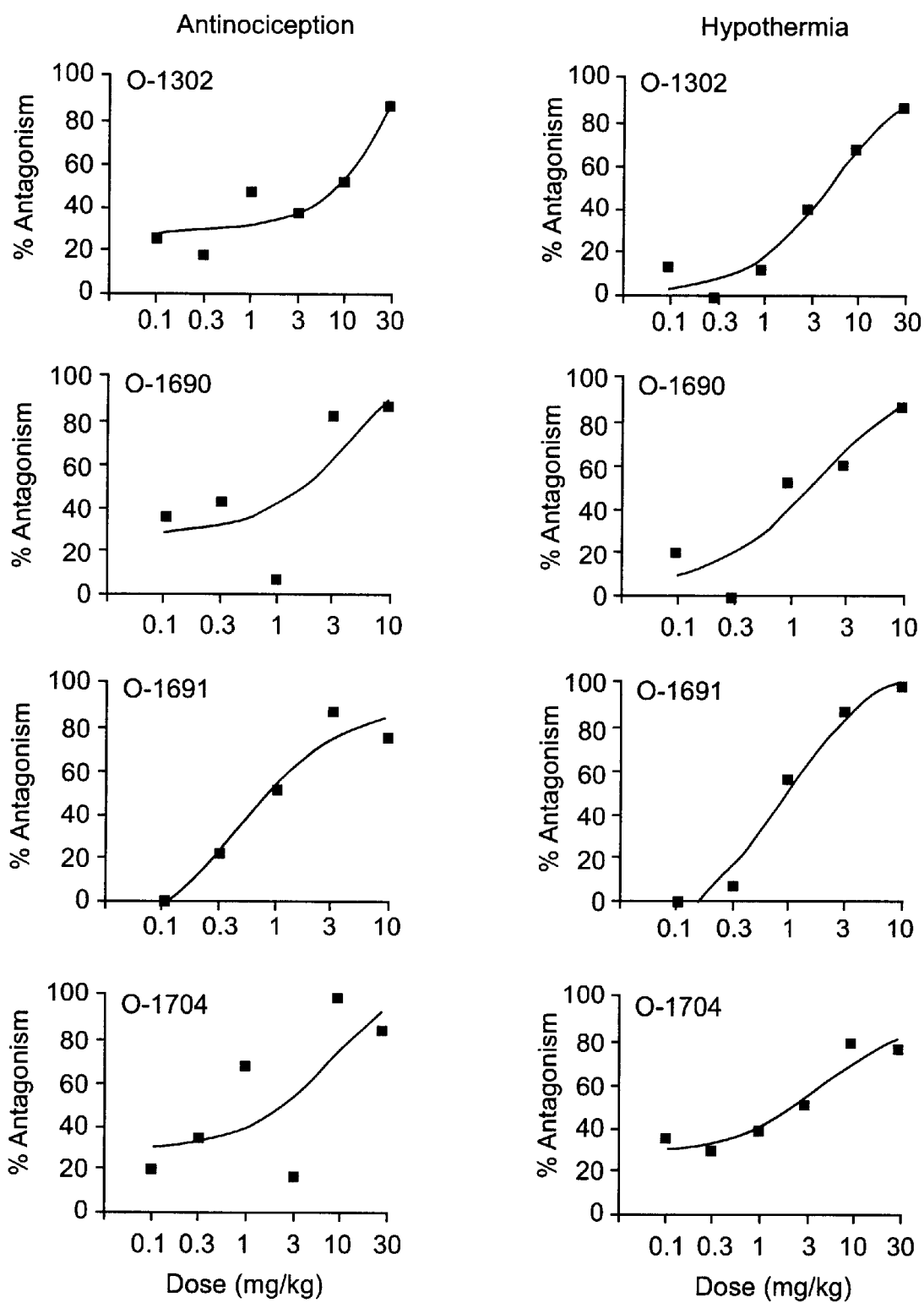
FIG. 6. Effects of 5-substituted pyrazole analogs of SR141716A on percentage antagonism of the antinociceptive (left panels) and hypothermic (right panels) effects of a 3 mg/kg (i.v.) dose of $\Delta^9$-THC in mice. Chemical structures of each analog are presented in Table 4 and AD$_{50}$'s are provided in Table 6.

Of all of the analogs, however, those with substitutions at position 5 (with or without concomitant substitution at position 4) produced the most consistent antagonist activity (Table 6). Retention of a phenyl group at position 5 and substitution of a pentyl or 1'-methylpentyl chain for the chloro in the p-chlorophenyl group of SR 141716 resulted in analogs that had high $CB_1$ binding affinity, lacked cannabinoid agonist activity in vivo, and were potent antagonists of the antinociceptive and hypothermic effects of $\Delta^9$-THC (FIG. 6). The phenyl group at this position appeared to be an important structural feature of the $CB_1$ binding affinity of these compounds, as O-1559 which retained a pentyl chain but lacked the phenyl group did not have good affinity. Given its low affinity, O-1559 was not tested for antagonist activity. Within the group of analogs that retained the phenyl group, differences in affinity and antagonist potency emerged. While branching of the pentyl by addition of a 1'-methyl (O-1690) did not affect affinity compared to the nonbranched pentyl substitution (O-1302), antagonist potency was increased approximately 3-fold for antinociception and hypothermia. A bromine or iodine substitution for the methyl at position 4 effected a similar increase in potency for antagonizing $\Delta^9$-THC-induced antinociception and hypothermia as did branching of the pentyl chain with no (iodine substitution, O-1704) or minor (bromine substitution, O-1691) increase in $CB_1$ binding affinity. In contrast, a hydrogen substitution at position 4 decreased affinity 10-fold and decreased maximal antagonism to 50–62%. Evaluation of antagonism of the locomotor suppressant effects of this series of analogs was problematic due to their prominent locomotor stimulatory effects, particularly when tested in combination with $\Delta^9$-THC (see Table 5).

SR141716A binds to $CB_1$ receptors and competitively antagonizes many of the $CB_1$ receptor-mediated effects of cannabinoids; hence, its structure would be expected to contain regions of overlap with those of cannabinoid agonists. An area of receptor recognition that is crucial for all known $CB_1$ agonists is a lipophilic side chain (e.g., THC and anandamides) or comparable moiety (e.g., nitrogen substituent of indole-derived cannabinoids) [Huffman et al., 1994; Martin et al., 1991; Thomas et al., 1996; Wiley et al., 1998]. Changes in the length, branching, and flexibility of this side chain affects $CB_1$ receptor binding affinity and in vivo potency of cannabinoid agonists (Compton et al., 1993; Huffman et al., 1997; Martin et al., 1999). A goal of this study was to determine whether any of the pyrazole substituents of SR141716A might correspond to the C3 side chain of $\Delta^9$-THC.

Molecular modeling suggests a possible superpositioning of the para-position of the 5-substituent in SR141716A with the pentyl side chain in $\Delta^9$-THC (Thomas et al., 1998). Structure-activity relationships (SAR) of SR141716A analogs presented here and elsewhere (Lan et al., 1999; Thomas et al., 1998) are consistent with this proposed alignment. Retention of the phenyl group is critical for receptor affinity and antagonism, as illustrated with O-1559 which had an alkyl group at position 5 rather than a phenyl. Substitution of the para-portion of the phenyl substituent is also important. Deletion of the p-chloro group (Lan et al., 1999) greatly decreased affinity whereas substitution of an alkyl group or an iodo/bromo (Thomas et al., 1998) enhanced affinity. Interestingly, lengthening of the pentyl side chain of $\Delta^9$-THC (Martin et al., 1999), methylation at the first or second carbon of the chain (Huffman et al., 1997), and halogenation at the terminal end of the chain (Charalambous et al., 1991) resulted in analogs that were agonists in vivo and that had enhanced $CB_1$ affinity compared to the parent compound.

Although all of the p-pentylphenyl analogs of SR141716A (Table 4) have good affinity for $CB_1$ receptors, none of these analogs show cannabinoid activity in vivo. Indeed, with the exception of O-1710 (the phenyl analog with the least affinity), all are potent antagonists of the antinociceptive and hypothermic effects of $\Delta^9$-THC. Presumably, they also will block activation of $CB_1$ receptors, although this hypothesis has yet to be tested in functional assays. Hence, the 5-substituent of pyrazole cannabinoids appears to be involved both in receptor recognition and in antagonism of receptor activation. Consistent with the hypothesis that this position is important for receptor recognition, Howlett et al. (2000) have shown that covalent binding of an azido or isothiocyano group to the p-position of the 5-phenyl ring of SR141716A irreversibly displaces $[H^3]CP$ 55,940 from its binding site.

Consistent with the proposed overlap of the C3 side chain of $\Delta^9$-THC and the 5-substituent of SR141716A, position 4 of the pyrazole core would correspond with either C2 or C4 of $\Delta^9$-THC (see FIG. 1). Addition of an iodine or bromine at this position of the p-pentylphenyl analog of SR141716A did not substantially alter affinity, whereas hydrogen substitution (O-1710) decreased it. By comparison, halogenation of C2 of $\Delta^9$-THC resulted in agonist analogs with decreased $CB_1$ affinity and halogenation of C4 produced inactive analogs with little affinity (Martin et al., 1993).

Another area likely to be involved in the antagonist actions of SR141716A is the 1-substituent. Thomas et al. (1998) have suggested that the 2,4-dichlorophenyl of SR141716A is its most unique area compared with $\Delta^9$-THC and that it may represent the antagonist conferring region. To date, results of SAR studies support this hypothesis. Manipulation of this area by removal of one or both of the chlorine atoms (present study; Lan et al., 1999), addition of a 3-chloro or 3- or 6-iodo group (Thomas et al., 1998), or substitution of an n-alkyl chain for the p-chloro group (present study) resulted in substantial decreases in $CB_1$ affinity and decreased potency or loss of antagonism. Of the analogs presented here, the branched p-1'-methylpropylphenyl analog (O-1253) had reasonable binding affinity and antagonist activity, although this analog had less affinity than SR141716A and it was not as potent an antagonist. Although the positioning of the two chlorine atoms is important in determining the $CB_1$ affinity of these 1-substituent analogs, presence of the 1-phenyl group is crucial for their antagonist activity. Replacement of the phenyl with an alkyl chain resulted in analogs that were partial agonists in a [$^{35}$S] GTPgammaS assay of G-protein activation (Houston et al., 1997). In contrast, analogs in which an alkyl chain was added to the phenyl group at p-position showed decreased affinity and were inactive in vivo (present study). Together, these findings demonstrate that small changes in the structure in the 1-substituent result in loss of antagonism, lending support to the hypothesis that this area is important in conferring receptor recognition and antagonist activity to pyrazole cannabinoids.

The 3-substituent of the pyrazole core, the fourth area of SR141716A that was manipulated in the present study, appears to be involved in receptor recognition, as analogs that were ethers, alkyl amides, ketones, alcohol or alkane showed greatly decreased $CB_1$ binding affinity. These results are in agreement with those of Lan et al. (1999). Only three of these analogs showed $CB_1$ binding affinity of less than 100 nM: napthalene, 4-fluorophenyl, and 2,4-difluorophenyl substitutions. The other 3-substituent analogs that showed reasonable binding affinity were some of the alkyl amides and ketones, with the best binding affinity exhibited by the n-pentyl and n-heptyl amides and the n-pentyl ketone. It is noteworthy that, in each of the pairs of alkylamides and ketones, the analog with n-pentyl substitution had the best affinity, suggesting that substituent length affected $CB_1$ receptor binding in both series. While none of the 3-substituent analogs that were tested completely blocked $\Delta^9$-THC's effects in all assays, several were agonists or partial agonists in vivo, although most were not as efficacious as $\Delta^9$-THC in producing the full profile of cannabimimetic effects. In addition, all of the active 3-substituent analogs were less potent than $\Delta^9$-THC, even though some of them had approximately the same affinity for the $CB_1$ receptor. Together, these results suggest that the 3-substituent region is involved in receptor recognition and agonist activity.

A final issue examined was the degree to which pyrazoles produce their effects through inverse agonism. SR141716A produces effects that have been considered possible indications of inverse agonism, including stimulation of locomotor activity in mice (Compton et al., 1996), inhibition of G protein-gated inwardly rectifying potassium (GIRK) channels in xenopus oocytes (McAllister et al., 1999), reduction in [$^{35}$S] GTPgammaS binding (Landsman et al., 1997), and increased twitch response in guinea pig ileum (Coutts et al., 2000). In the present study, substantial locomotor stimulation was observed with some analogs, particularly those with 1- and 5-substituent substitutions. Since these analogs also showed the most antagonist activity, it is tempting to speculate that this antagonism may have resulted from inverse agonism; however, several observations argue against this hypothesis. First, $\Delta^9$-THC produces a biphasic effect on locomotor activity with stimulation at lower doses and suppression at higher doses (Evans et al., 1976). It is possible that any locomotor stimulation may be related to the agonist or partial agonist activity of some of these analogs. Second, the locomotor stimulation does not appear to be correlated with the $CB_1$ affinity of these analogs nor with their potency for antagonizing the in vivo effects of $\Delta^9$-THC. For example, the greatest degree of stimulation was produced by O-1559; yet, this analog did not have good $CB_1$ affinity nor was it an antagonist in vivo. These results suggest that the stimulatory effect that we observed with some of these analogs is not strongly related to action at the $CB_1$ receptor.

In summary, this study was undertaken in order to examine the pharmacological profile of various SR141716A analogs in which the 1-, 3-, 4-, and 5-positions of the pyrazole core were replaced by substituents known to impart potent agonist activity in tetrahydrocannabinols. Our results suggest that, while all three positions are important for receptor recognition, the effects of the positions differ with respect to receptor activation. The 3-position appears to be involved in agonism and receptor activation. In contrast, the 1-, 4-, and 5-positions seem to be involved in antagonism. Further, the present evaluation of locomotor stimulatory effects does not support the hypothesis that the antagonist activity of pyrazole cannabinoids is related to inverse agonism. In conclusion, the present results suggest that binding and activation of the cannabinoid $CB_1$ receptor are separable events and that the structural properties of 1- and 5-substituents are primarily responsible for the antagonist activity of SR141716A.

It will be apparent to one skilled in the area that various substitution and modification may be made to the invention disclosed herein without departing form the scope and the spirit of the invention. Accordingly, the scope of the invention should be determined by the appended claims and their legal equivalents, rather than the examples given.

REFERENCES

Adams I B, Ryan W, Singer M, Thomas B F, Compton D R, Razdan R K, and Martin B R. *J Pharmacol Exp Ther.* 1995, 273, 1172–1181.

Bradford M M. *Anal Biochem.* 1976, 72, 248–254.

Charalambous A, Lin S, Marciniak G, Banijamali A, Friend F L, Compton D R, Martin B R, and Makriyannis A. *Pharmacol Biochem Behav.* 1991, 40, 509–512.

Compton D R, Aceto M D, Lowe J, and Martin B R. *J Pharmacol Exp Ther.* 1996, 277, 586–594.

Compton D R, Gold L H, Ward S J, Balster R L, and Martin B R. *J Pharmacol Exp Ther.* 1992, 263, 1118–1126.

Compton D R, Rice K C, De Costa B R, Razdan R K, Melvin L S, Johnson M R, and Martin B R. *J Pharmacol Exp Ther.* 1993, 265, 218–226.

Coutts A A, Brewster N, Ingram T, Razdan R K, and Pertwee R G. *J Pharmacol.* 2000, 129, 645Devane W A, Dysarz III F A, Johnson M R, Melvin L S, and Howlett A C. *Mol Pharmacol.* 1988, 34, 605–613.

Dewey W L, Harris L S, Howes J F, and Nuite J A. *J Pharmacol Exp Ther.* 1970, 175, 435–442.

Dutta A K, Sard H, Ryan W, Razdan R K, Compton D R, and Martin B R. *Med Chem Res.* 1995, 5, 54–62.

Evans M A, Harbison R D, Brown D J, and Forney R B. *Psychopharmacology.* 1976, 50, 245GriffithW P, Ley S V, Whitcombe G P, and White A D. *Chem Commun.* 1987, 1625–1627.

Houston D B, Lan R, Pigg J J, Wilken G, Howlett A C, and Makriyannis A. in *International Cannabinoid Research Society: 1997 Symposium on the Cannabinoids*, p. 28, International Cannabinoid Research Society, Burlington, Vt. 1997.

Howlett A C, Wilken G H, Pigg J J, Houston D B, Lan R, Liu Q, and Makriyannis A. *J Neurochem.* 2000, 74, 2174–2181.

Huffman J W, Dai D, Martin B R, and Compton D R. *Biomed Chem Lett.* 1994, 4, 563–566.

Huffman J W, Lainton J A H, Banner W K, Duncan Jr S G, Jordan R D, Yu S, Dai D, Martin B R, Wiley J L, and Compton D R. *Tetrahedron.* 1997, 53, 1557–1576.

Lan R, Liu Q, Fan P, Lin S, Fernando S R, Mccallion D, Pertwee R, and Makriyannis A. *J Med Chem.* 1999, 42, 769–776.

Landsman R S, Burkey T H, Consroe P, Roeske W R, and Yamamura H I. *Eur J Pharmacol.* 1997, 334, R1Lichtman A H, Wiley J L, Lavecchia K L, Neviaser S T, Arthur D B, Wilson D M, and Martin B R. *Eur J Pharmacol.* 1998.357,139–148.

Martin B R, Compton D R, Semus S F, Lin S, Marciniak G, Grzybowska J, Charalambous A, and Makriyannis A. *Pharmacol Biochem Behav.* 1993, 46, 295–301.

Martin B R, Compton D R, Thomas B F, Prescott W R, Little P J, Razdan R K, Johnson M R, Melvin L S, Mechoulam R, and Ward S J. *Pharmacol Biochem Behav.* 1991. 40, 471–478.

Martin B R, Jefferson R, Winckler R, Wiley J L, Huffman J W, Crocker P J, Saha B, and Razdan R K. *J Pharmacol Exp Ther.* 1999, 290, 1065–1079.

Mechoulam R, Hanus L, and Martin B R. *Biochem Pharm.* 1994. 48(8), p. 1537–1544.

Mcallister S D, Griffin G, Satin L S, and Abood M E. *J Pharmacol Exp Ther.* 7999, 291, 618Murray W V and Wachter M P. *J. Heterocyclic Chem.* 1989, 26,1389–1392.

Pacheco M, Childers S R, Arnold R, Casiano F, and Ward S J. 1991, *J Pharmacol Exp Ther.* 257, 170–183.

Rinaldi-Carmona M, Barth F, H é aulme M, Shire D, Calandra B, Congy C, Martinez S, Maruani J, N é liat G, Caput D, Ferrara P, Soubri é P, Breli é re J C, and Le Fur G. *FEBS Lett.* 1994, 350, 240–244.

Smith P B, Compton D R, Welch S P, Razdan R K, Mechoulam R, and Martin B R. *J Pharmacol Exp Ther.* 1994, 270, 219–227.

Thomas B F, Adams I B, S W, Martin B R, and Razdan R K. *J Med Chem.* 1996, 39, 471–479.

Thomas B F, Gilliam A F, Burch D F, Roche M J, and Seltzman H H. *J Pharmacol Exp Ther.* 1998, 285, 285–292.

Wiley J L. *Pharmacol Biochem Behav.* 1999, 64, 257–260.

Wiley J L, Compton D R, Dai D, Lainton J A H, Phillips M, Huffman J W, and Martin B R. *J Pharmacol Exp Ther.* 1998, 285, 995–1004.

TABLE 1

Pharmacological Effects of 1-(2,4-Dichlorophenyl)-4-Methyl-5-(4-Chlorophenyl)-1H-Pyrazoles with Cyclic 3-Substituents.

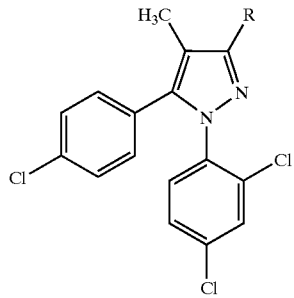

| Compound | R | $K_i$ (nM) | SA | TF | RT |
|---|---|---|---|---|---|
| $\Delta^9$-THC[a] | | 41 | 0.92 | 2.7 | 2.5 |
| SR141716A | (acetamido-piperidine) | 6.2[b] | >30[c] | >30[c] | >30[c] |
| O-848 | (ethoxyethyl-piperidine) | 2450 ± 720 | 69% (10)[a] | NT | NT |
| O-849 | (ethoxymethyl-phenyl) | 108 ± 9 | >30 | >30 | −4 (30)[#] |
| O-850 | (ethoxymethyl-tetrahydropyran) | 351 ± 34 | >10 | NT | NT |

TABLE 1-continued

Pharmacological Effects of 1-(2,4-Dichlorophenyl)-4-Methyl-5-(4-Chlorophenyl)-1H-Pyrazoles with Cyclic 3-Substituents.

| Compound | R | $K_i$ (nM) | SA | TF | RT |
|---|---|---|---|---|---|
| O-852 | ethoxymethyl-naphthalen-1-yl | 78 ± 10 | >10 | >10 | >10 |
| O-853 | ethoxymethyl-cyclohexyl | 388 ± 32 | NT | NT | NT |
| O-869 | ethoxymethyl-(4-methoxyphenyl) | 194 ± 11 | >30 | >30 | >30 |
| O-870 | ethoxymethyl-(4-chlorophenyl) | 109 ± 9 | 66% (30)[#] | >30 | −3 (30)[#] |
| O-889 | ethoxymethyl-(4-fluorophenyl) | 54 ± 2 | 20 (17–25) | 67% (30)[#] | 40 (31–52) |
| O-890 | ethoxymethyl-anthracen-9-yl | 379 ± 38 | >10 | >10 | >10 |
| O-909 | ethoxymethyl-naphthalen-2-yl | 216 ± 29 | >30 | >30 | >30 |
| O-910 | ethoxymethyl-(4-methylnaphthalen-1-yl) | 143 ± 15 | >30 | >30 | >30 |

TABLE 1-continued

Pharmacological Effects of 1-(2,4-Dichlorophenyl)-4-Methyl-5-(4-Chlorophenyl)-1H-Pyrazoles with Cyclic 3-Substituents.

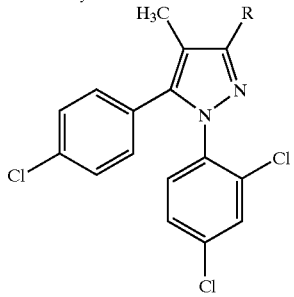

| Compound | R | $K_i$ (nM) | SA | TF | RT |
|---|---|---|---|---|---|
| O-1043 | | 53 ± 9 | >30 | >30 | >30 |

For Tables 1–4:
indicates the maximal effect that was produced by the analog and the dose (mg/kg) at which it occurred in parentheses.
"> dose" indicates that 50% activity was not achieved at this dose (mg/kg), which was the highest dose of the compound that was tested. All ED50's are expressed as μmol/kg (with 95% confidence limits in parentheses).
SA = suppression of spontaneous activity;
MPE = % maximum possible antinociceptive effect in tail flick assay;
RT = rectal temperature.
[a]from Wiley et al., 1998.
[b]from Thomas et al., 1998.
[c]from Compton et al., 1996.

TABLE 2

Pharmacological Effects of 1-(2,4-Dichlorophenyl)-4-Methyl-5-(4-Chlorophenyl)-1H-Pyrazoles with Carbon Chain 3-Substituents.

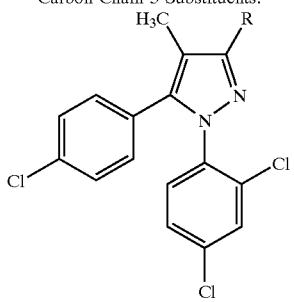

| Compound | R | $K_i$ (nM) | SA | TF | RT |
|---|---|---|---|---|---|
| O-1269 | | 32 ± 5 | 11 (7–19) | 21* (9–49) | 11 (8–16) |
| O-1270 | | 48 ± 12 | 27 (19–44) | 20 (9–54) | 12 (10–15) |
| O-1271 | | 82 ± 10 | >30 | >30 | >30 |

TABLE 2-continued

Pharmacological Effects of 1-(2,4-Dichlorophenyl)-4-Methyl-5-(4-Chlorophenyl)-1H-Pyrazoles with Carbon Chain 3-Substituents.

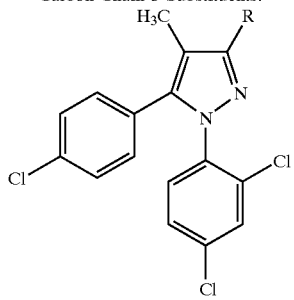

| Compound | R | $K_i$ (nM) | SA | TF | RT |
|---|---|---|---|---|---|
| O-1272 | (heptanoyl, C(=O)-hexyl) | 221 ± 36 | 54% (30)[#] | >30 | −3 (30)[#] |
| O-1398 | C(=O)NH-CH₂CH₂-F | 852 ± 175 | 7* (not calculated) | 13 (10–18) | 8 (5–12) |
| O-1399 | C(=O)NH-propyl | 167 ± 32 | 9 (5–17) | 24 (16–36) | 10 (7–16) |
| O-1876 | CH(OH)-pentyl | 657 ± 21 | >30 | >30 | >30 |
| O-1877 | heptyl | 422 ± 40 | >30 | >30 | >30 |

*indicates an estimated $ED_{50}$ due to the fact that the dose-effect curve was not linear.

TABLE 3

Pharmacological Effects of N-(Piperidin-1-yl)-5-(4-Chloro-phenyl)-3-carboxamide-4-Methyl-1H Pyrazole with various 1-Substituents.

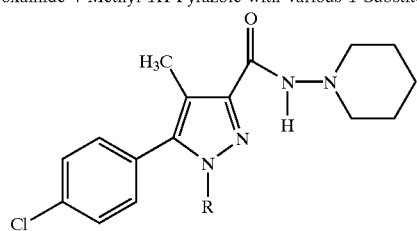

| Compound | R | $K_i$ (nM) | SA | TF | RT |
|---|---|---|---|---|---|
| O-1253 | 4-(sec-butyl)phenyl | 47 ± 2 | >30 | >30 | >30 |

TABLE 3-continued

Pharmacological Effects of N-(Piperidin-1-yl)-5-(4-Chloro-phenyl)-3-carboxamide-4-Methyl-1H Pyrazole with various 1-Substituents.

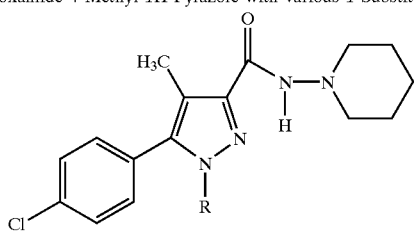

| Compound | R | $K_i$ (nM) | SA | TF | RT |
|---|---|---|---|---|---|
| O-1254 | 4-butylphenyl | 226 ± 4 | >30 | >30 | >30 |

TABLE 3-continued

Pharmacological Effects of N-(Piperidin-1-yl)-5-(4-Chloro-phenyl)-3-carboxamide-4-Methyl-1H Pyrazole with various 1-Substituents.

| Compound | R | $K_i$ (nM) | SA | TF | RT |
|---|---|---|---|---|---|
| O-1255 | 4-pentylphenyl | 433 ± 103 | >30 | >30 | >30 |
| O-1300 | phenyl | 150 ± 20 | >30 | >30 | >30 |

TABLE 4

Pharmacological Effects of N-(Piperidin-1-yl)-1-(2,4-Dichloro-phenyl)-3-carboxamide-4-Methyl-1H-Pyrazole with various 5- and 4-Substituents.

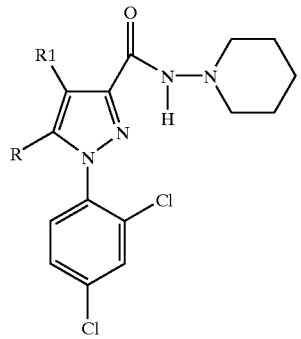

| Compound | R | R1 | $K_i$ (nM) | SA | TF | RT |
|---|---|---|---|---|---|---|
| O-1302 | 5-phenylpentyl | $CH_3$ | 2.1 ± 0.08 | >30 | >30 | >30 |
| O-1559 | 2-methylpentyl | $CH_3$ | 233 ± 3 | >30 | >30 | >30 |
| O-1690 | 1-methyl-4-phenylbutyl | $CH_3$ | 2.6 ± 0.13 | >30 | >30 | >30 |

TABLE 4-continued

Pharmacological Effects of N-(Piperidin-1-yl)-1-(2,4-Dichloro-phenyl)-3-carboxamide-4-Methyl-1H-Pyrazole with various 5- and 4-Substituents.

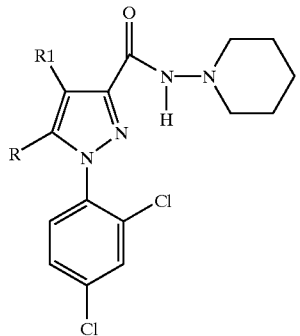

| Compound | R | R1 | $K_i$ (nM) | SA | TF | RT |
|---|---|---|---|---|---|---|
| O-1691 | pentylphenyl[a] | Br | 1.5 ± 0.22 | >30 | >30 | >30 |
| O-1704 | pentylphenyl[a] | I | 2.2 ± 0.15 | >30 | >30 | >30 |
| O-1710 | pentylphenyl[a] | H | 27 ± 0.86 | >30 | >30 | >30 |

[a]Point of attachment to the pyrazole core at R.

TABLE 5

Maximum Stimulation and Inhibition of Spontaneous Locomotor Activity by Pyrazole Analogs

| | Compound Alone | | Compound with 3 mg/kg Δ⁹-THC | |
|---|---|---|---|---|
| Compound | Max stim (dose) | Max % inhibit (dose) | Max stim (dose) | Max % inhibit (dose) |
| 3-substituent | | | | |
| O-848 | None (10) | 69% (10) | NT | NT |
| O-849 | 25% (10) | 48% (30) | NT | NT |
| O-850 | None (10) | 43% (10) | NT | NT |
| O-852 | 52% (1) | stim at 1, 3 & 10 | NT | NT |
| O-853 | NT | NT | NT | NT |
| O-869 | None (30) | 31% (30) | NT | NT |
| O-870 | None (30) | 46% (30) | NT | NT |
| O-889 | 31% (1) | 96% (30) | None (3) | 72% (3) |
| O-890 | 4% (30) | stim at 30 | NT | NT |
| O-909 | None (30) | 3% (30) | NT | NT |
| O-910 | 4% (30) | stim at 30 | NT | NT |
| O-1043 | 24% (3) | 49% (30) | None (3 & 10) | 88% (3) |
| O-1269 | 7% (1) | 87% (30) | None (1, 3 & 10) | 91% (10) |
| O-1270 | 29% (3) | 80% (30) | None (10) | 87% (10) |
| O-1271 | 54% (3) | 7% (30) | None (3 & 10) | 58% (3) |
| O-1272 | 17% (3) | 54% (30) | NT | NT |
| O-1398 | None (3, 10 & 30) | 97% (10) | NT | NT |
| O-1399 | None (3, 10 & 30) | 100% (30) | NT | NT |
| O-1876 | None (30) | 11% (30) | NT | NT |
| O-1877 | 5% (30) | stim at 30 | NT | NT |
| 1-substituent | | | | |
| O-1253 | 73% (30) | stim at 1, 3, 10 & 30 | 50% (10) | 89% (0.1) |
| O-1254 | 29% (30) | stim at 3, 10 & 30 | 13% (30) | stim at 10 |
| O-1255 | None (3, 10 & 30) | 20% (10) | None (10) | 65% (10) |
| O-1300 | 54% (30) | stim at 30 | NT | NT |
| 4 and/or 5 substituent | | | | |

TABLE 5-continued

Maximum Stimulation and Inhibition of Spontaneous Locomotor Activity by Pyrazole Analogs

| | Compound Alone | | Compound with 3 mg/kg $\Delta^9$-THC | |
|---|---|---|---|---|
| Compound | Max stim (dose) | Max % inhibit (dose) | Max stim (dose) | Max % inhibit (dose) |
| O-1302 | 2% (10) | 26% (3) | 107% (30) | 74% (0.3) |
| O-1559 | 118% (30) | stim at 3, 10 & 30 | NT | NT |
| O-1690 | 18% (30) | 24% (10) | 39% (10) | 88% (0.3) |
| O-1691 | 66% (1) | 15% (3) | 150% (3) | 91% (0.1) |
| O-1704 | 57% (1) | 19% (30) | 49% (10) | 85% (0.3) |
| O-1710 | 4% (1) | 42% (10) | None (0.3, 1, 3, & 10) | 82% (10) |

Maximum % stimulation and % inhibition produced by pyrazole analogs tested alone (left panel) and tested in combination with 3 mg/kg $\Delta^9$-THC (right panel). Dose(s) [mg/kg] at which the effect occurred are given in parentheses.

TABLE 6

Maximum % Antagonism or $AD_{50}$ by Pyrazole Analogs

| Compound | Dose Range Tested (mg/kg) | SA | % MPE | RT |
|---|---|---|---|---|
| SR141716A | 0.1–3 | 100% (3) | 96% (0.1) | 0.34 (0.26–0.44) |
| 3-substituent | | | | |
| O-852 | NT | NT | NT | NT |
| O-889 | 3 | 2% (3) | 40% (3) | 11% (3) |
| O-1043 | 3 & 10 | None (3, 10) | 51% (10) | None (3, 10) |
| O-1269 | 1–10 | 38% (3) | 66% (3) | 43% (1) |
| O-1270 | 1–10 | None (10) | 37% (3) | 26% (1) |
| O-1271 | 3 & 10 | 77% (10) | 65% (10) | 36% (3) |
| 1-substituent | | | | |
| O-1253 | 0.1–10 | 97% (1) | 3.3 (1.9–6.0) | 4.7 (2.6–8.3) |
| O-1254 | 10 & 30 | stimulation | 52% (30) | 31% (10) |
| O-1255 | 10 | 0% (10) | 13% (10) | 14% (10) |
| 5- and/or 4-substituent | | | | |
| O-1302 | 0.1–30 | 91% (1) | 6.4 (2–not avail) | 8.6 (4.4–16.4) |
| O-1690 | 0.1–10 | 65% (1) | 1.8 (0.6–5.3) | 2.7 (1.5–4.7) |
| O-1691 | 0.1–10 | 6% (0.3) | 1.9 (1.1–3.2) | 1.8 (1.2–2.7) |
| O-1704 | 0.1–30 | 65% (3) | 1.8 (0.7–4.3) | 2.1 (1.0–4.3) |
| O-1710 | 0.3–10 | 50% (3) | 62% (10) | 51% (1) |

SA = suppression of spontaneous activity; MPE = % maximum possible antinociceptive effect in tail flick assay; RT = rectal temperature. $AD_{50}$'s expressed as γmol/kg (with 95% confidence limits in parentheses) are provided whenever % antagonism is dose-responsive. When % antagonism was not dose-responsive, values are expressed as maximum % antagonism across all doses tested. Dose(s) [mg/kg] at which the maximum antagonist effect occurred are given in parentheses. For SA, stimulation (i.e., maximum antagonism >100%) was not included in % antagonism calculations.

What is claimed is:

1. A pyrazole derivative, and pharmaceutically acceptable salts thereof, having the formula I:

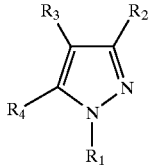

wherein
  $R_1$ is 2,4-dichlorophenyl;
  $R_2$ is carboxamide-4-methyl-1H-pyrazole
  $R_3$ is a methyl, a hydrogen or a halogen; and
  $R_4$ is a $C_{1-8}$ alkyl or a phenyl that is unsubstituted or substituted one or more times by a halogen, or a $C_{1-7}$ alkyl;
  provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;
  further provided that $R_3$ is other than a methyl, where $R_6$ is a piperidine.

2. The pyrazole derivative, and pharmaceutically acceptable salts thereof, of claim 1, wherein
  $R_3$ is a methyl or a halogen; and
  $R_4$ is phenyl that is substituted once by an n-pentyl or sec-hexyl.

3. The pyrazole derivative, and pharmaceutical acceptable salts thereof, of claim 2, wherein said halogen is selected from the group consisting of Br and I.

4. The pyrazole derivative, and pharmaceutically acceptable salts thereof, of claim 1, wherein
  $R_3$ is a methyl;
  $R_4$ is a 4-chlorophenyl; and
  $R_6$ is an n-heptyl or a fluoroalkyl.

5. The pyrazole derivative, and pharmaceutical acceptable salts thereof, of claim 3, wherein said fluoroalkyl is a 1-fluoroethyl of formula —$CH_2CH_2F$.

6. The pyrazole derivative, and pharmaceutically acceptable salts thereof, of claim 1, wherein
  $R_3$ is a methyl;
  $R_4$ is a 4-chlorophenyl;
  $R_5$ is a 4-fluorophenyl or a 2,4-difluorophenyl; and m is 1.

7. A method for treating a condition mediated by interacting with CB1 cannabinoid receptor, comprising administering to a patient in need thereof an effective amount of a pyrazole derivative, or pharmaceutically acceptable salts thereof, having the formula I:

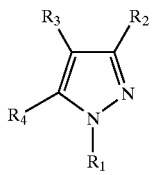

wherein
  $R_1$ is 2,4-dichlorophenyl;
  $R_2$ is carboxamide-4-methyl-1H-pyrazole
  $R_3$ is a methyl, a hydrogen or a halogen; and
  $R_4$ is a $C_{1-8}$ alkyl or a phenyl that is unsubstituted or substituted one or more times by a halogen, or a $C_{1-7}$ alkyl;
  provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;
  further provided that $R_3$ is other than a methyl, where $R_6$ is a piperidine.

8. The method for treating condition mediated by interacting with CB1 cannabinoid receptor of claim 7, wherein
  $R_3$ is a methyl or a halogen; and
  $R_4$ is phenyl that is substituted once by an n-pentyl or sec-hexyl.

9. The method for treating condition mediated by interacting with CB1 cannabinoid receptor of claim 8, wherein said halogen is selected from the group consisting of Br and I.

10. The method for treating condition mediated by interacting with CB1 cannabinoid receptor of claim 7, wherein
  $R_3$ is a methyl;
  $R_4$ is a 4-chlorophenyl; and
  $R_6$ is an n-heptyl or a fluoroalkyl.

11. The method for treating condition mediated by interacting with CB1 cannabinoid receptor of claim 10, wherein said fluoroalkyl is a 1-fluoroethyl of formula —$CH_2CH_2F$.

12. The method for treating condition mediated by interacting with CB1 cannabinoid receptor of claim 7, wherein
  $R_3$ is a methyl;
  $R_4$ is a 4-chlorophenyl; and
  $R_5$ is a 4-fluorophenyl or a 2,4-difluorophenyl; and
  m is 1.

13. A pyrazole derivative, and pharmaceutically acceptable salts thereof, having the formula I:

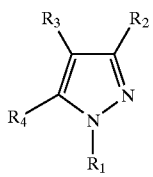

wherein
  $R_1$ is a phenyl that is unsubstituted or substituted one or more times by a halogen, or a $C_{1-7}$ alkyl;
  $R_2$ is
    an ether of formula
      —$CH_2$—O—$(CH_2)_m$—$R_5$, where $R_5$ is a heterocyclic, a $C_{4-7}$ cycloalkyl, or an aryl, and m is 1 or 2;
    an amide of formula —C(O)NH$R_6$, where $R_6$ is a $C_{1-8}$ alkyl, a $C_{1-6}$ haloalkyl, or a piperidine,
    a ketone of formula —C(O)$R_7$, where $R_7$ is a $C_{1-6}$ alkyl, or
    an alcohol of formula —CH(OH)$R_8$, where $R_8$ is $C_{1-6}$ alkyl, (with the proviso that $R_2$ is not carboxamide-4-methyl-1H-pyrazole);
  $R_3$ is a methyl, a hydrogen or a halogen; and
  $R_4$ is a $C_{1-8}$ alkyl or a phenyl that is unsubstituted or substituted one or more times by a halogen, or a $C_{1-7}$ alkyl;
  provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;
  further provided that $R_3$ is other than a methyl, where $R_6$ is a piperidine.

14. A pyrazole derivative, and pharmaceutically acceptable salts thereof, having the formula I:

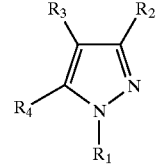

wherein
  $R_1$ is a phenyl that is unsubstituted or substituted one or more times by a halogen, or a $C_{1-7}$ alkyl (with the proviso that $R_1$ is not 2,4-dichlorophenyl);
  $R_2$ is an ether of formula —$CH_2$—O—$(CH_2)_m$—$R_5$, where $R_5$ is a heterocyclic, a $C_{4-7}$ cycloalkyl, or an aryl, and m is 1 or 2;
    an amide of formula —C(O)NH$R_6$, where $R_6$ is a $C_{1-8}$ alkyl, a $C_{1-6}$ haloalkyl, or a piperidine,
    a ketone of formula —C(O)$R_7$, where $R_7$ is a $C_{1-6}$ alkyl, or
    an alcohol of formula —CH(OH)$R_8$, where $R_8$ is $C_{1-6}$ alkyl;
  $R_3$ is a methyl, a hydrogen or a halogen; and
  $R_4$ is a $C_{1-8}$ alkyl or a phenyl that is unsubstituted or substituted one or more times by a halogen, or a $C_{1-7}$ alkyl;
  provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;
  further provided that $R_3$ is other than a methyl, where $R_6$ is a piperidine.

15. A method for treating a condition mediated by interacting with CB1 cannabinoid receptor, comprising administering to a patient in need thereof an effective amount of a pyrazole derivative, or pharmaceutically acceptable salts thereof, having the formula I:

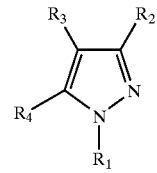

wherein
  $R_1$ is a phenyl that is unsubstituted or substituted one or more times by a halogen, or a $C_{1-7}$ alkyl (with the proviso that $R_1$ is not 2,4-dichlorophenyl);

$R_2$ is an ether of formula —$CH_2$—O—$(CH_2)_m$—$R_5$, where $R_5$ is a heterocyclic, a $C_{4-7}$ cycloalkyl, or an aryl, and m is 1 or 2;

an amide of formula —$C(O)NHR_6$, where $R_6$ is a $C_{1-8}$ alkyl, a $C_{1-6}$ haloalkyl, or a piperidine, a ketone of formula —$C(O)R_7$, where $R_7$ is a $C_{1-6}$ alkyl, or an alcohol of formula —$CH(OH)R_8$, where $R_8$ is $C_{1-6}$ alkyl;

$R_3$ is a methyl, a hydrogen or a halogen; and $R_4$ is a $C_{1-8}$ alkyl or a phenyl that is unsubstituted or substituted one or more times by a halogen, or a $C_{1-7}$ alkyl;

provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;

further provided that $R_3$ is other than a methyl, where $R_6$ is a piperidine.

16. A method for treating a condition mediated by interacting with CB1 cannabinoid receptor, comprising administering to a patient in need thereof an effective amount of a pyrazole derivative, or pharmaceutically acceptable salts thereof, having the formula I:

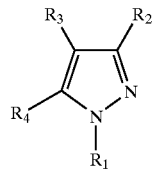

wherein $R_1$ is a phenyl that is unsubstituted or substituted one or more times by a halogen, or a $C_{1-7}$ alkyl;

$R_2$ is an ether of formula —$CH_2$—O—$(CH_2)_m$—$R_5$, where $R_5$ is a heterocyclic, a $C_{4-7}$ cycloalkyl, or an aryl, and m is 1 or 2;

an amide of formula —$C(O)NHR_6$, where $R_6$ is a $C_{1-8}$ alkyl, a $C_{1-6}$ haloalkyl, or a piperidine, a ketone of formula —$C(O)R_7$, where $R_7$ is a $C_{1-6}$ alkyl, or an alcohol of formula —$CH(OH)R_8$, where $R_8$ is $C_{1-6}$ alkyl (with the proviso that $R_2$ is not carboxamide-4-methyl-1H-pyrazole);

$R_3$ is a methyl, a hydrogen or a halogen; and $R_4$ is a $C_{1-8}$ alkyl or a phenyl that is unsubstituted or substituted one or more times by a halogen, or a $C_{1-7}$ alkyl;

provided that $R_6$ is other than a $C_{1-3}$ alkyl, where $R_1$ and $R_4$ are together or independently a phenyl that is unsubstituted or substituted one or more times by a halogen, or an unbranched $C_{1-3}$ alkyl;

further provided that $R_3$ is other than a methyl, where $R_6$ is a piperidine.

17. A pyrazole derivative according to claim 1, selected from the group consisting of compounds O-1302, O-1559, O-1690, O-1691, O-1704 and O-1710.

18. A pyrazole derivative according to claim 13, selected from the group consisting of compounds O-1269, O-1270, O-1271, O-1272, O-1398, O-1399, O-1876, O-1877, O-848, O-849, O-850, O-852, O-853, O-869, O-870, O-889, O-890, O-909, O-910 and O-1043.

* * * * *